United States Patent
Yang et al.

(10) Patent No.: US 7,374,877 B2
(45) Date of Patent: *May 20, 2008

(54) AMPLIFICATION OF HIV-1 GAG SEQUENCES FOR DETECTION OF SEQUENCES ASSOCIATED WITH DRUG-RESISTANCE MUTATIONS

(75) Inventors: Yeasing Y. Yang, San Diego, CA (US); Steven T. Brentano, Santee, CA (US); Odile Babola, Decines (FR); Nathalie Tran, Dagneux (FR); Guy Vernet, Albigny sur Saone (FR)

(73) Assignees: Gen-Probe Incorporated, San Diego, CA (US); BioMerieux S.A., Marcy-l'Etoile (FR)

( * ) Notice: Subject to any disclaimer, the term of this patent is extended or adjusted under 35 U.S.C. 154(b) by 195 days.

This patent is subject to a terminal disclaimer.

(21) Appl. No.: 11/145,272

(22) Filed: Jun. 3, 2005

(65) Prior Publication Data

US 2005/0227227 A1 Oct. 13, 2005

Related U.S. Application Data

(62) Division of application No. 10/425,975, filed on Apr. 28, 2003, now Pat. No. 6,946,254, which is a division of application No. 09/944,036, filed on Aug. 31, 2001, now Pat. No. 6,582,920.

(60) Provisional application No. 60/229,790, filed on Sep. 1, 2000.

(51) Int. Cl.
*C07H 21/00* (2006.01)
*C12N 15/49* (2006.01)

(52) U.S. Cl. .............. 435/5; 435/6; 435/974; 536/24.3; 536/24.32; 536/24.33

(58) Field of Classification Search .............. None
See application file for complete search history.

(56) References Cited

U.S. PATENT DOCUMENTS

| | | |
|---|---|---|
| 5,075,211 A | 12/1991 | Cosand et al. |
| 5,185,439 A | 2/1993 | Arnold, Jr. et al. |
| 5,384,242 A | 1/1995 | Oakes |
| 5,399,491 A | 3/1995 | Kacian et al. |
| 5,427,930 A | 6/1995 | Birkenmeyer et al. |
| 5,457,025 A | 10/1995 | Collins et al. |
| 5,459,243 A | 10/1995 | Acevedo et al. |
| 5,472,840 A | 12/1995 | Stefano |
| 5,554,516 A | 9/1996 | Kacian et al. |
| 5,582,989 A | 12/1996 | Caskey et al. |

(Continued)

FOREIGN PATENT DOCUMENTS

DE 19850186 A1 5/2000

(Continued)

OTHER PUBLICATIONS

Agrawal et al., "Oligodeoxynucleotide phosphoramidates and phosphorothioates as inhibitors of human immunodeficiency virus", Proc. Nat. Acad. Sci. USA, Oct. 1988, 85(19):7079-83.

(Continued)

*Primary Examiner*—Mary E. Mosher
*Assistant Examiner*—Stuart W. Snyder
(74) *Attorney, Agent, or Firm*—Christine A. Gritzmacher

(57) ABSTRACT

Sequences of nucleic acid oligonucleotides for amplifying different portions of gag and pol genes of HIV-1 and for detecting such amplified nucleic acid sequences are disclosed. Methods of amplifying and detecting HIV-1 nucleic acid in a biological sample using the amplification oligonucleotides specific for gag and pol target sequences are disclosed.

24 Claims, 2 Drawing Sheets

U.S. PATENT DOCUMENTS

| | | | |
|---|---|---|---|
| 5,599,662 | A | 2/1997 | Respess |
| 5,602,240 | A | 2/1997 | De Mesmaeker et al. |
| 5,629,158 | A | 5/1997 | Uhlen |
| 5,629,413 | A | 5/1997 | Peterson et al. |
| 5,658,737 | A | 8/1997 | Nelson et al. |
| 5,684,147 | A | 11/1997 | Agrawal et al. |
| 5,688,637 | A | 11/1997 | Moncany et al. |
| 5,693,535 | A | 12/1997 | Draper et al. |
| 5,700,922 | A | 12/1997 | Cook |
| 5,712,385 | A | 1/1998 | McDonough et al. |
| 5,840,480 | A | 11/1998 | Guertler et al. |
| 5,849,494 | A | 12/1998 | Heneine et al. |
| 5,856,088 | A * | 1/1999 | McDonough et al. .......... 435/5 |
| 5,861,242 | A | 1/1999 | Chee et al. |
| 5,919,701 | A | 7/1999 | Peterson et al. |
| 5,962,665 | A | 10/1999 | Kroeger et al. |
| 5,972,596 | A | 10/1999 | Pavlakis et al. |
| 5,998,593 | A | 12/1999 | Huff et al. |
| 6,001,558 | A | 12/1999 | Backus et al. |
| 6,001,977 | A | 12/1999 | Chang et al. |
| 6,111,068 | A | 8/2000 | Zimmerman et al. |
| 6,117,635 | A | 9/2000 | Nazarenko et al. |
| 6,127,115 | A | 10/2000 | Ragland et al. |
| 6,174,668 | B1 | 1/2001 | Cummins et al. |
| 6,221,578 | B1 | 4/2001 | de Béthune et al. |
| 6,265,152 | B1 | 7/2001 | Dunn et al. |
| 6,270,975 | B1 | 8/2001 | Simon et al. |
| 6,277,561 | B1 | 8/2001 | Guertler et al. |
| 6,451,530 | B1 | 9/2002 | Hawkins |
| 6,492,110 | B1 | 12/2002 | Hahn |
| 6,503,705 | B1 | 1/2003 | Kozal et al. |
| 6,582,920 | B2 | 6/2003 | Yang et al. |
| 6,589,920 | B2 | 7/2003 | Okada et al. |
| 6,610,476 | B1 | 8/2003 | Chang et al. |
| 6,649,749 | B2 | 11/2003 | McDonough et al. |
| 6,656,706 | B2 | 12/2003 | Pavlakis |
| 6,696,291 | B2 | 2/2004 | Shiver et al. |
| 6,794,498 | B2 | 9/2004 | Pavlakis et al. |
| 6,800,463 | B1 | 10/2004 | Larder et al. |
| 6,946,254 | B2 * | 9/2005 | Yang et al. .................... 435/6 |

FOREIGN PATENT DOCUMENTS

| | | | |
|---|---|---|---|
| EP | 0345375 | A1 | 12/1989 |
| EP | 0403333 | A2 | 12/1990 |
| EP | 0516540 | A1 | 12/1992 |
| EP | 0591914 | A2 | 4/1994 |
| EP | 0617132 | A2 | 9/1994 |
| EP | 0709466 | A2 | 5/1996 |
| EP | 0727497 | A1 | 8/1996 |
| EP | 0747488 | A1 | 12/1996 |
| EP | 0806484 | A2 | 11/1997 |
| EP | 0854197 | A2 | 7/1998 |
| EP | 0887427 | A2 | 12/1998 |
| EP | 0890642 | A2 | 1/1999 |
| EP | 1 087 020 | A2 | 3/2001 |
| WO | WO 9008840 | A * | 8/1990 |
| WO | WO 91/08308 | A1 | 6/1991 |
| WO | WO 93/13121 | A1 | 7/1993 |
| WO | WO 94/16108 | A1 | 7/1994 |
| WO | WO 95/03407 | A2 | 2/1995 |
| WO | WO 9521938 | A1 * | 8/1995 |
| WO | WO 97/37005 | A1 | 10/1997 |
| WO | WO 98/00563 | A1 | 1/1998 |
| WO | WO 98/50583 | A1 | 11/1998 |
| WO | WO 99/07898 | A1 | 2/1999 |
| WO | WO 99/16910 | A1 | 4/1999 |
| WO | WO 99/61666 | A1 | 12/1999 |
| WO | WO 01/04360 | A2 | 1/2001 |
| WO | WO 01/04361 | A2 | 1/2001 |
| WO | WO01/07661 | A2 | 2/2001 |
| WO | WO01/36614 | A2 | 5/2001 |
| WO | WO 01/89509 | A2 | 11/2001 |
| WO | WO02/04494 | A2 | 1/2002 |

OTHER PUBLICATIONS

Billyard et al., "Detection of HIV-1 RNA from Plasma Specimens Using Transcription Mediated Amplification", Clin. Chem., 1995, 41(11):1684 (Abstract).

Billyard et al., "Early Detection of HIV-1 RNA with Transcription-Mediated Amplification", Transfusion, 1997, 37(9):S386 (Abstract).

Bush et al., "Detection of Human Immunodeficiency Virus Type 1 RNA in Plasma Samples from High-Risk Pediatric Patients by Using the Self-Sustained Sequence Replication Reaction", J. Clin. Microbiol., Feb. 1992, 30(2):281-6.

De Baar et al., "Design and Evaluation of a Human Immunodeficiency Virus Type 1 RNA Assay Using Nucleic Acid Sequence-Based Amplification Technology Able To Quantify Both Group M and O Viruses by Using the Long Terminal Repeat as Target", J. Clin. Microbiol., Jun. 1999, 37(6):1813-18.

Debyser et al., "Failure to Quantify Viral Load with Two of the Three Commercial Methods in a Pregnant Woman Harboring an HIV Type 1 Subtype G Strain", Aids Res. Hum. Retroviruses, Mar. 1998, 14(5):453-59.

Delord et al., "Analysis of HIV-1 expression in vivo with in situ hybridization and the polymerase chain reaction", Mol. Cell. Probes, Jun. 1992, 6(3):215-21.

Garduno et al., "Early detection of HIV-1 RNA from sero-conversion panels using Gen-Probe's transcription-mediated amplification", Clin. Chem., 1997, 43(11):2221 (Abstract).

Goodenow et al., "HIV-1 Isolates Are Rapidly Evolving Quasispecies: Evidence for Viral Mixtures and Preferred Nucleotide Substitutions", J. Acquir. Immune Defic. Syndr. 1989, 2(4):344-52.

Hewlett et al., "Co-amplification of multiple regions of the HIV-1 genome by the polymerase chain reaction: potential use in multiple diagnosis", Oncogene, Sep. 1989, 4(9):1149-51.

Kumar et al., "Detection of human immunodeficiency virus (HIV) and human lymphotropic virus (HTLV) type I or II dual infections by polymerase chain reaction", Oncogene, Dec. 1989, 4(12):1533-35.

Leparc et al., "Nucleic Acid Testing for Screening Donor Blood", Infect. Med., 2000, 17(5):320.

Matthews et al., "Analytical Strategies for the Use of DNA Probes", Anal. Biochem., Feb. 1988, 169(1):1-25.

O'Shea et al., "Problems in the Interpretation of HIV-1 Viral Load Assays Using Commercial Reagents", J. Med. Virol., Jun. 2000, 61(2):187-94.

Ou et al., "DNA Amplification for Direct Detection of HIV-1 in DNA of Peripheral Blood Mononuclear Cells", Science, Jan. 1988, 239(4837):295-7.

Pieniazek et al., Identification of mixed HIV-1/HIV-2 infections in Brazil by polymerase chain reaction, AIDS, Nov. 1991, 5(11):1293-9.

Van Gemen et al., "The One-tube Quantitative HIV-1 RNA NASBA: Precision, Accuracy, and Application", PCR Methods and Appl., Feb. 1995, 4(4):S177-84.

Williams et al., "Quantitative Competitive Polymerase Chain Reaction: Analysis of Amplified Products of the HIV-1 gag Gene by Capillary Electrophoresis with Laser-Induced Fluorescence Detection", Anal. Biochem., Apr. 1996, 236(1):146-52.

Yang et al., "Detection of HIV-1 RNA Subtypes with Transcription-Mediated Amplification", Abstr. Gen. Meet. Am. Soc. Microbiol., 1997, 97:538 (Abstract).

Zimmerman et al., "Rapid Nonradioactive Detection of HIV-1 RNA from a Single-Cell Equivalent by Reverse Transcription PCR with Nested Primers", BioTechniques, Nov. 1993, 15(5):806-8.

* cited by examiner

SEQUENCE LISTING

```
<160> NUMBER OF SEQ ID NOS: 70

<210> SEQ ID NO 1
<211> LENGTH: 29
<212> TYPE: DNA
```

```
<213> ORGANISM: Artificial Sequence
<220> FEATURE:
<223> OTHER INFORMATION: T7 promoter

<400> SEQUENCE: 1
gaaatttaat acgactcact atagggaga                                29

<210> SEQ ID NO 2
<211> LENGTH: 37
<212> TYPE: DNA
<213> ORGANISM: Artificial Sequence
<220> FEATURE:
<223> OTHER INFORMATION: T7 promoter

<400> SEQUENCE: 2
gaaattaata cgactcacta tagggagacc acattga                       37

<210> SEQ ID NO 3
<211> LENGTH: 32
<212> TYPE: DNA
<213> ORGANISM: Artificial Sequence
<220> FEATURE:
<223> OTHER INFORMATION: T7 promoter

<400> SEQUENCE: 3
aatttaatac gactcactat agggagacca ca                            32

<210> SEQ ID NO 4
<211> LENGTH: 33
<212> TYPE: DNA
<213> ORGANISM: Artificial Sequence
<220> FEATURE:
<223> OTHER INFORMATION: T7 promoter

<400> SEQUENCE: 4
gaaattaata cgactcacta tagggagacc aca                           33

<210> SEQ ID NO 5
<211> LENGTH: 50
<212> TYPE: DNA
<213> ORGANISM: Artificial Sequence
<220> FEATURE:
<223> OTHER INFORMATION: primer for Gag target sequence
<220> FEATURE:
<221> NAME/KEY: promoter
<222> LOCATION: (1)..(29)
<223> OTHER INFORMATION:

<400> SEQUENCE: 5
gaaatttaat acgactcact atagggagag tggctccttc tgataatgct         50

<210> SEQ ID NO 6
<211> LENGTH: 54
<212> TYPE: DNA
<213> ORGANISM: Artificial Sequence
<220> FEATURE:
<223> OTHER INFORMATION: primer for Gag target sequence
<220> FEATURE:
<221> NAME/KEY: misc_feature
<222> LOCATION: (46)..(46)
<223> OTHER INFORMATION: Nebularine
<220> FEATURE:
<221> NAME/KEY: promoter
<222> LOCATION: (1)..(33)
<223> OTHER INFORMATION:

<400> SEQUENCE: 6
gaaattaata cgactcacta tagggagacc acattgatgc ccttcnttgc caca    54
```

```
<210> SEQ ID NO 7
<211> LENGTH: 52
<212> TYPE: DNA
<213> ORGANISM: Artificial Sequence
<220> FEATURE:
<223> OTHER INFORMATION: primer for Protease target sequence
<220> FEATURE:
<221> NAME/KEY: promoter
<222> LOCATION: (1)..(32)
<223> OTHER INFORMATION:

<400> SEQUENCE: 7
aatttaatac gactcactat agggagacca cagccatcca ttcctggctt ta          52

<210> SEQ ID NO 8
<211> LENGTH: 50
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(32)
<223> OTHER INFORMATION:

<400> SEQUENCE: 8
aatttaatac gactcactat agggagacca cagctgccct atttctaagt             50

<210> SEQ ID NO 9
<211> LENGTH: 54
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 9
gaaattaata cgactcacta tagggagacc acattgataa atttgatatg tcca        54

<210> SEQ ID NO 10
<211> LENGTH: 55
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 10
gaaattaata cgactcacta tagggagacc acactgttag ctgccccatc tacat       55

<210> SEQ ID NO 11
<211> LENGTH: 21
<212> TYPE: DNA
<213> ORGANISM: Artificial Sequence
<220> FEATURE:
<223> OTHER INFORMATION: primer for Gag target sequence

<400> SEQUENCE: 11
gtggctcctt ctgataatgc t                                            21
```

<210> SEQ ID NO 12
<211> LENGTH: 17
<212> TYPE: DNA
<213> ORGANISM: Artificial Sequence
<220> FEATURE:
<223> OTHER INFORMATION: primer for Gag target sequence
<220> FEATURE:
<221> NAME/KEY: misc_feature
<222> LOCATION: (9)..(9)
<223> OTHER INFORMATION: Nebularine

<400> SEQUENCE: 12
tgcccttcnt tgccaca                                              17

<210> SEQ ID NO 13
<211> LENGTH: 20
<212> TYPE: DNA
<213> ORGANISM: Artificial Sequence
<220> FEATURE:
<223> OTHER INFORMATION: primer for Protease target sequence

<400> SEQUENCE: 13
gccatccatt cctggcttta                                           20

<210> SEQ ID NO 14
<211> LENGTH: 18
<212> TYPE: DNA
<213> ORGANISM: Artificial Sequence
<220> FEATURE:
<223> OTHER INFORMATION: primer for Reverse Transcriptase target
      sequence

<400> SEQUENCE: 14
gctgccctat ttctaagt                                             18

<210> SEQ ID NO 15
<211> LENGTH: 21
<212> TYPE: DNA
<213> ORGANISM: Artificial Sequence
<220> FEATURE:
<223> OTHER INFORMATION: primer for Reverse Transcriptase target
      sequence

<400> SEQUENCE: 15
ttgataaatt tgatatgtcc a                                         21

<210> SEQ ID NO 16
<211> LENGTH: 22
<212> TYPE: DNA
<213> ORGANISM: Artificial Sequence
<220> FEATURE:
<223> OTHER INFORMATION: primer for Reverse Transcriptase target
      sequence

<400> SEQUENCE: 16
ctgttagctg ccccatctac at                                        22

<210> SEQ ID NO 17
<211> LENGTH: 19
<212> TYPE: DNA
<213> ORGANISM: Artificial Sequence
<220> FEATURE:
<223> OTHER INFORMATION: primer for Gag target sequence

<400> SEQUENCE: 17
gacaccaagg aagctttag                                            19

<210> SEQ ID NO 18
<211> LENGTH: 22
<212> TYPE: DNA
<213> ORGANISM: Artificial Sequence
<220> FEATURE:
<223> OTHER INFORMATION: primer for Gag target sequence

<400> SEQUENCE: 18
tgggattaaa taaaatagta ag                                           22

<210> SEQ ID NO 19
<211> LENGTH: 20
<212> TYPE: DNA
<213> ORGANISM: Artificial Sequence
<220> FEATURE:
<223> OTHER INFORMATION: primer for Protease target sequence

<400> SEQUENCE: 19
aaggaaggac accaaatgaa                                              20

<210> SEQ ID NO 20
<211> LENGTH: 20
<212> TYPE: DNA
<213> ORGANISM: Artificial Sequence
<220> FEATURE:
<223> OTHER INFORMATION: primer for Reverse Transcriptase target
      sequence

<400> SEQUENCE: 20
gccattgaca gaagaaaaaa                                              20

<210> SEQ ID NO 21
<211> LENGTH: 17
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: misc_feature
<222> LOCATION: (15)..(15)
<223> OTHER INFORMATION: Nebularine

<400> SEQUENCE: 21
ttagaaatag ggcanca                                                 17

<210> SEQ ID NO 22
<211> LENGTH: 22
<212> TYPE: DNA
<213> ORGANISM: Artificial Sequence
<220> FEATURE:
<223> OTHER INFORMATION: primer for Reverse Transcriptase target
      sequence

<400> SEQUENCE: 22
acttaatagc agaaatacag aa                                           22

<210> SEQ ID NO 23
<211> LENGTH: 22
<212> TYPE: DNA
<213> ORGANISM: Artificial Sequence
<220> FEATURE:
<223> OTHER INFORMATION: probe for amplified Gag sequence

<400> SEQUENCE: 23
tcaggccata tcacctagaa ct                                           22

```
<210> SEQ ID NO 24
<211> LENGTH: 22
<212> TYPE: DNA
<213> ORGANISM: Artificial Sequence
<220> FEATURE:
<223> OTHER INFORMATION: probe for amplified Gag sequence of HIV-1
      subtype A

<400> SEQUENCE: 24
ttgaatgcat gggtgaaggt aa                                              22

<210> SEQ ID NO 25
<211> LENGTH: 25
<212> TYPE: DNA
<213> ORGANISM: Artificial Sequence
<220> FEATURE:
<223> OTHER INFORMATION: probe for amplified Gag sequence
<220> FEATURE:
<221> NAME/KEY: misc_feature
<222> LOCATION: (12)..(12)
<223> OTHER INFORMATION: Nebularine

<400> SEQUENCE: 25
gttttggctg angcaatgag tcagg                                           25

<210> SEQ ID NO 26
<211> LENGTH: 18
<212> TYPE: DNA
<213> ORGANISM: Artificial Sequence
<220> FEATURE:
<223> OTHER INFORMATION: probe for amplified Protease sequence

<400> SEQUENCE: 26
gtaggaccta cacctgtc                                                   18

<210> SEQ ID NO 27
<211> LENGTH: 25
<212> TYPE: DNA
<213> ORGANISM: Artificial Sequence
<220> FEATURE:
<223> OTHER INFORMATION: probe for amplified Reverse Transcriptase
      sequence

<400> SEQUENCE: 27
gggcctgaaa atccatacaa tactc                                           25

<210> SEQ ID NO 28
<211> LENGTH: 22
<212> TYPE: DNA
<213> ORGANISM: Artificial Sequence
<220> FEATURE:
<223> OTHER INFORMATION: probe for amplified Reverse Transcriptase
      sequence
<220> FEATURE:
<221> NAME/KEY: misc_feature
<222> LOCATION: (18)..(18)
<223> OTHER INFORMATION: Nebularine

<400> SEQUENCE: 28
agctggactg tcaatganat ac                                              22

<210> SEQ ID NO 29
<211> LENGTH: 25
<212> TYPE: DNA
<213> ORGANISM: Artificial Sequence
<220> FEATURE:
<223> OTHER INFORMATION: probe for amplified Reverse Transcriptase
``` sequence

<400> SEQUENCE: 29
gcatagtaat atggggaaag actcc                                             25

<210> SEQ ID NO 30
<211> LENGTH: 56
<212> TYPE: DNA
<213> ORGANISM: Artificial Sequence
<220> FEATURE:
<223> OTHER INFORMATION: Capture oligonucleotide

<400> SEQUENCE: 30
gctggaataa cttctgcttc tattttaaaa aaaaaaaaa aaaaaaaaaa aaaaaa            56

<210> SEQ ID NO 31
<211> LENGTH: 57
<212> TYPE: DNA
<213> ORGANISM: Artificial Sequence
<220> FEATURE:
<223> OTHER INFORMATION: Capture oligonucleotide

<400> SEQUENCE: 31
tctgctgtcc ctgtaataaa cccgtttaaa aaaaaaaaa aaaaaaaaaa aaaaaaa           57

<210> SEQ ID NO 32
<211> LENGTH: 55
<212> TYPE: DNA
<213> ORGANISM: Artificial Sequence
<220> FEATURE:
<223> OTHER INFORMATION: Capture oligonucleotide

<400> SEQUENCE: 32
actgacgctc tcgcacccat cttttaaaaa aaaaaaaaa aaaaaaaaaa aaaaa             55

<210> SEQ ID NO 33
<211> LENGTH: 54
<212> TYPE: DNA
<213> ORGANISM: Artificial Sequence
<220> FEATURE:
<223> OTHER INFORMATION: primer for Gag target sequence
<220> FEATURE:
<221> NAME/KEY: promoter
<222> LOCATION: (1)..(33)
<223> OTHER INFORMATION:

<400> SEQUENCE: 33
gaaattaata cgactcacta tagggagacc acagtggctc cttctgataa tgct            54

<210> SEQ ID NO 34
<211> LENGTH: 53
<212> TYPE: DNA
<213> ORGANISM: Artificial Sequence
<220> FEATURE:
<223> OTHER INFORMATION: primer for Gag target sequence
<220> FEATURE:
<221> NAME/KEY: promoter
<222> LOCATION: (1)..(33)
<223> OTHER INFORMATION:
<220> FEATURE:
<221> NAME/KEY: misc_feature
<222> LOCATION: (45)..(45)
<223> OTHER INFORMATION: Nebularine

<400> SEQUENCE: 34
gaaattaata cgactcacta tagggagacc acatgatgcc cttcnttgcc aca             53

```
<210> SEQ ID NO 35
<211> LENGTH: 53
<212> TYPE: DNA
<213> ORGANISM: Artificial Sequence
<220> FEATURE:
<223> OTHER INFORMATION: primer for Gag target sequence
<220> FEATURE:
<221> NAME/KEY: promoter
<222> LOCATION: (1)..(33)
<223> OTHER INFORMATION:

<400> SEQUENCE: 35
gaaattaata cgactcacta tagggagacc acagggtggc tccttctgat aat         53

<210> SEQ ID NO 36
<211> LENGTH: 53
<212> TYPE: DNA
<213> ORGANISM: Artificial Sequence
<220> FEATURE:
<223> OTHER INFORMATION: primer for Gag target sequence
<220> FEATURE:
<221> NAME/KEY: promoter
<222> LOCATION: (1)..(33)
<223> OTHER INFORMATION:

<400> SEQUENCE: 36
gaaattaata cgactcacta tagggagacc acatgatgcc cttctttgcc aca         53

<210> SEQ ID NO 37
<211> LENGTH: 53
<212> TYPE: DNA
<213> ORGANISM: Artificial Sequence
<220> FEATURE:
<223> OTHER INFORMATION: primer for Protease target sequence
<220> FEATURE:
<221> NAME/KEY: promoter
<222> LOCATION: (1)..(33)
<223> OTHER INFORMATION:

<400> SEQUENCE: 37
gaaattaata cgactcacta tagggagacc acagccatcc attcctggct tta         53

<210> SEQ ID NO 38
<211> LENGTH: 53
<212> TYPE: DNA
<213> ORGANISM: Artificial Sequence
<220> FEATURE:
<223> OTHER INFORMATION: primer for Protease target sequence
<220> FEATURE:
<221> NAME/KEY: promoter
<222> LOCATION: (1)..(33)
<223> OTHER INFORMATION:

<400> SEQUENCE: 38
gaaattaata cgactcacta tagggagacc acaccatcca ttcctggctt taa         53

<210> SEQ ID NO 39
<211> LENGTH: 52
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 39
gaaattaata cgactcacta tagggagacc acagctgccc tatttctaag tc          52
```

<210> SEQ ID NO 40
<211> LENGTH: 51
<212> TYPE: DNA
<213> ORGANISM: Artificial Sequence
<220> FEATURE:
<223> OTHER INFORMATION: primer for Reverse Transcriptase sequence
<220> FEATURE:
<221> NAME/KEY: promoter
<222> LOCATION: (1)..(29)
<223> OTHER INFORMATION:

<400> SEQUENCE: 40
aaattaatac gactcactat agggagacta tgctgccctg tttctaagtc a          51

<210> SEQ ID NO 41
<211> LENGTH: 51
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 41
gaaattaata cgactcacta tagggagacc acagctgccc tatttctaag t          51

<210> SEQ ID NO 42
<211> LENGTH: 53
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 42
gaaattaata cgactcacta tagggagacc acatcttgat aaatttgata tgt        53

<210> SEQ ID NO 43
<211> LENGTH: 52
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 43
gaaattaata cgactcacta tagggagacc acatttcctg ttttcagatt tt         52

<210> SEQ ID NO 44
<211> LENGTH: 55
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)

<223> OTHER INFORMATION:

<400> SEQUENCE: 44
gaaattaata cgactcacta tagggagacc acacctgtta gctgccccat ctaca      55

<210> SEQ ID NO 45
<211> LENGTH: 55
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: promoter
<222> LOCATION: (1)..(33)
<223> OTHER INFORMATION:

<400> SEQUENCE: 45
gaaattaata cgactcacta tagggagacc acatccctgt tagctgcccc atcta      55

<210> SEQ ID NO 46
<211> LENGTH: 21
<212> TYPE: DNA
<213> ORGANISM: Artificial Sequence
<220> FEATURE:
<223> OTHER INFORMATION: primer for Gag target sequence

<400> SEQUENCE: 46
gtggctcctt ctgataatgc t      21

<210> SEQ ID NO 47
<211> LENGTH: 20
<212> TYPE: DNA
<213> ORGANISM: Artificial Sequence
<220> FEATURE:
<223> OTHER INFORMATION: primer for Gag target sequence

<400> SEQUENCE: 47
gggtggctcc ttctgataat      20

<210> SEQ ID NO 48
<211> LENGTH: 20
<212> TYPE: DNA
<213> ORGANISM: Artificial Sequence
<220> FEATURE:
<223> OTHER INFORMATION: primer for Gag target sequence
<220> FEATURE:
<221> NAME/KEY: misc_feature
<222> LOCATION: (12)..(12)
<223> OTHER INFORMATION: Nebularine

<400> SEQUENCE: 48
tgatgccctt cnttgccaca      20

<210> SEQ ID NO 49
<211> LENGTH: 20
<212> TYPE: DNA
<213> ORGANISM: Artificial Sequence
<220> FEATURE:
<223> OTHER INFORMATION: primer for Gag target sequence

<400> SEQUENCE: 49
tgatgccctt ctttgccaca      20

<210> SEQ ID NO 50
<211> LENGTH: 20
<212> TYPE: DNA

```
<213> ORGANISM: Artificial Sequence
<220> FEATURE:
<223> OTHER INFORMATION: primer for Protease target sequence

<400> SEQUENCE: 50
gccatccatt cctggcttta                                               20

<210> SEQ ID NO 51
<211> LENGTH: 20
<212> TYPE: DNA
<213> ORGANISM: Artificial Sequence
<220> FEATURE:
<223> OTHER INFORMATION: primer for Protease target sequence

<400> SEQUENCE: 51
ccatccattc ctggctttaa                                               20

<210> SEQ ID NO 52
<211> LENGTH: 19
<212> TYPE: DNA
<213> ORGANISM: Artificial Sequence
<220> FEATURE:
<223> OTHER INFORMATION: primer for Reverse Transcriptase target
      sequence

<400> SEQUENCE: 52
gctgccctat ttctaagtc                                                19

<210> SEQ ID NO 53
<211> LENGTH: 23
<212> TYPE: DNA
<213> ORGANISM: Artificial Sequence
<220> FEATURE:
<223> OTHER INFORMATION: primer for Reverse Transcriptase target
      sequence

<400> SEQUENCE: 53
tatgctgccc tatttctaag tca                                           23

<210> SEQ ID NO 54
<211> LENGTH: 18
<212> TYPE: DNA
<213> ORGANISM: Artificial Sequence
<220> FEATURE:
<223> OTHER INFORMATION: primer for Reverse Transcriptase target
      sequence

<400> SEQUENCE: 54
gctgccctat ttctaagt                                                 18

<210> SEQ ID NO 55
<211> LENGTH: 20
<212> TYPE: DNA
<213> ORGANISM: Artificial Sequence
<220> FEATURE:
<223> OTHER INFORMATION: primer for Reverse Transcriptase target
      sequence

<400> SEQUENCE: 55
tcttgataaa tttgatatgt                                               20

<210> SEQ ID NO 56
<211> LENGTH: 19
<212> TYPE: DNA
<213> ORGANISM: Artificial Sequence
<220> FEATURE:
<223> OTHER INFORMATION: primer for Reverse Transcriptase target
```

-continued

```
                                 sequence

<400> SEQUENCE: 56
tttcctgttt tcagattt                                                    19

<210> SEQ ID NO 57
<211> LENGTH: 22
<212> TYPE: DNA
<213> ORGANISM: Artificial Sequence
<220> FEATURE:
<223> OTHER INFORMATION: primer for Reverse Transcriptase target
      sequence

<400> SEQUENCE: 57
cctgttagct gccccatcta ca                                               22

<210> SEQ ID NO 58
<211> LENGTH: 22
<212> TYPE: DNA
<213> ORGANISM: Artificial Sequence
<220> FEATURE:
<223> OTHER INFORMATION: primer for Reverse Transcriptase target
      sequence

<400> SEQUENCE: 58
tccctgttag ctgccccatc ta                                               22

<210> SEQ ID NO 59
<211> LENGTH: 19
<212> TYPE: DNA
<213> ORGANISM: Artificial Sequence
<220> FEATURE:
<223> OTHER INFORMATION: primer for Gag target sequence
<220> FEATURE:
<221> NAME/KEY: misc_feature
<222> LOCATION: (16)..(16)
<223> OTHER INFORMATION: Nebularine

<400> SEQUENCE: 59
gacaccaagg aagctntag                                                   19

<210> SEQ ID NO 60
<211> LENGTH: 22
<212> TYPE: DNA
<213> ORGANISM: Artificial Sequence
<220> FEATURE:
<223> OTHER INFORMATION: primer for Gag target sequence
<220> FEATURE:
<221> NAME/KEY: misc_feature
<222> LOCATION: (5)..(5)
<223> OTHER INFORMATION: Nebularine

<400> SEQUENCE: 60
tgggnttaaa taaaatagta ag                                               22

<210> SEQ ID NO 61
<211> LENGTH: 20
<212> TYPE: DNA
<213> ORGANISM: Artificial Sequence
<220> FEATURE:
<223> OTHER INFORMATION: primer for Protease target sequence

<400> SEQUENCE: 61
gaaggacacc aaatgaagga                                                  20

<210> SEQ ID NO 62
<211> LENGTH: 20
```

```
<212> TYPE: DNA
<213> ORGANISM: Artificial Sequence
<220> FEATURE:
<223> OTHER INFORMATION: primer for Protease target sequence
<220> FEATURE:
<221> NAME/KEY: misc_feature
<222> LOCATION: (6)..(6)
<223> OTHER INFORMATION: Inosine

<400> SEQUENCE: 62
aagganggac accaaatgaa                                                      20

<210> SEQ ID NO 63
<211> LENGTH: 22
<212> TYPE: DNA
<213> ORGANISM: Artificial Sequence
<220> FEATURE:
<223> OTHER INFORMATION: primer for Reverse Transcriptase target
      sequence

<400> SEQUENCE: 63
gaagaaaaaa taaaagcatt ag                                                   22

<210> SEQ ID NO 64
<211> LENGTH: 19
<212> TYPE: DNA
<213> ORGANISM: Artificial Sequence
<220> FEATURE:
<223> OTHER INFORMATION: primer for Reverse Transcriptase target
      sequence

<400> SEQUENCE: 64
gccattgaca gaagaaaaa                                                       19

<210> SEQ ID NO 65
<211> LENGTH: 20
<212> TYPE: DNA
<213> ORGANISM: Artificial Sequence
<220> FEATURE:
<223> OTHER INFORMATION: primer for Reverse Transcriptase target
      sequence

<400> SEQUENCE: 65
gccattgaca gaagagaaaa                                                      20

<210> SEQ ID NO 66
<211> LENGTH: 22
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: misc_feature
<222> LOCATION: (5)..(5)
<223> OTHER INFORMATION: Nebularine
<220> FEATURE:
<221> NAME/KEY: misc_feature
<222> LOCATION: (12)..(12)
<223> OTHER INFORMATION: Nebularine

<400> SEQUENCE: 66
ggcancatag ancaaaaata ga                                                   22

<210> SEQ ID NO 67
<211> LENGTH: 24
<212> TYPE: DNA
<213> ORGANISM: Artificial Sequence
<220> FEATURE:
```

-continued

```
<223> OTHER INFORMATION: primer for Reverse Transcriptase target
      sequence

<400> SEQUENCE: 67
agacttaata gcagaaatac agaa                                          24

<210> SEQ ID NO 68
<211> LENGTH: 22
<212> TYPE: DNA
<213> ORGANISM: Artificial Sequence
<220> FEATURE:
<223> OTHER INFORMATION: primer for Reverse Transcriptase target
      sequence
<220> FEATURE:
<221> NAME/KEY: misc_feature
<222> LOCATION: (15)..(15)
<223> OTHER INFORMATION: Nebularine

<400> SEQUENCE: 68
acttaatagc agaantacag aa                                            22

<210> SEQ ID NO 69
<211> LENGTH: 24
<212> TYPE: DNA
<213> ORGANISM: Artificial Sequence
<220> FEATURE:
<223> OTHER INFORMATION: primer for Gag target sequence

<400> SEQUENCE: 69
gttttggctg agcaatgagt cagg                                          24

<210> SEQ ID NO 70
<211> LENGTH: 23
<212> TYPE: DNA
<213> ORGANISM: Artificial Sequence
<220> FEATURE:
<223> OTHER INFORMATION: probe for amplified Gag sequence

<400> SEQUENCE: 70
tggagaaaat tagtagattt cag                                           23
```

AMPLIFICATION OF HIV-1 GAG SEQUENCES FOR DETECTION OF SEQUENCES ASSOCIATED WITH DRUG-RESISTANCE MUTATIONS

RELATED APPLICATION

This application is a divisional of application Ser. No. 10/425,975, filed April 28,2003, now U.S. Pat. No. 6,946, 254 which is a divisional of application Ser. No. 09/944,036, filed Aug. 31, 2001, now U.S. Pat. No. 6,582,920, which claims the benefit under 35 U.S.C. 119(e) of provisional application no. 60/229,790, filed Sep. 1, 2000, all of which are incorporated by reference.

FIELD OF THE INVENTION

This invention relates to diagnostic detection of Human Immunodeficiency Virus (HIV-1), and more particularly relates to compositions and assays for detecting HIV-1 nucleic acid sequences using nucleic acid amplification and detection of amplified sequences, particularly sequences related to development of HIV-1 drug resistance.

BACKGROUND OF THE INVENTION

HIV-1 is the causative agent of acquired immunodeficiency syndrome (AIDS). Early detection of HIV-1 infection is important for determining effective treatment of the infection and to avoid transmission of the infectious virus in body fluids, even before the infected individual manifests symptoms. Early detection of the presence of HIV-1 nucleic acid sequences in infected tissue or body fluid can lead to earlier treatment and steps to prevent spread of the virus to others. To be effective in early diagnosis, reagents and procedures to detect HIV-1 nucleic acid sequences must be able to detect relatively low numbers of viral copies. in the tested sample (e.g., a few hundred copies per ml of plasma). Furthermore, diagnostic methods that provide additional information about the HIV-1 present in an infected individual, such as the HIV-1 subtype and/or mutational changes associated with viral drug-resistance, are useful for prognosis.

Drug-resistance mutations (substitutions, deletions or insertions of one or more nucleic acid bases) have been found in HIV-1 patients who have been treated with drugs and have experienced a resurgence of HIV-1 proliferation and symptoms. Such mutations, which result in a phenotypic change whereby the virus becomes resistant to an antiretroviral drug, have found in the gag gene, often affecting protease cleavage sites, and the pol gene, in both the protease and the reverse transcriptase (RT) coding regions (Gingeras et al., 1991, *J. Infect. Dis.* 164(6):1066-1074; Richman et al., 1991, *J. Infect. Dis.* 164(6):1075-1081; Schinazi et al., 1993, *Antimicrob. Agents Chemother.* 37(4): 875-881; Najera et al., 1994, *AIDS Res. Hum. Retroviruses* 10(11):1479-1488; Eastman et al., 1995, *J. AIDS Hum. Retrovirol.* 9(3):264-273; Frenkel et al., 1995, *J. Clin. Microbiol.* 33(2):342-347; Shirasaka et al., 1995, Proc. Natl. Acad. Sci. USA 92(6):2398-2402; Leal et al., 1996, *Eur. J. Clin. Invest.* 26(6):476-480; Cleland et al., 1996, *J. AIDS Hum. Retrovirol.* 12(1):6-18; Schmit et al., 1996, *AIDS* 10(9):995-999; Vasudevechari et al., 1996, *Antimicrob. Agents Chemother.* 40(11):2535-2541; Winslow et al., 1996, *AIDS* 10(11):1205-1209; Fontenot et al., *Virology* 190(1):1-10; Cornelissen et al., 1997, *J. Virol.* 71(9):6348-6358; Ives et al., 1997, *J. Antimicrob. Chemother.* 39(6):771-779).

Information on viral mutations present in an HIV-1 infected patient can be used by a clinician to determine appropriate treatment, such as whether to begin or maintain the patient on a particular antiretroviral therapy. Moreover, continued testing of patient samples that permits characterization of the HIV-1 during treatment can indicate emergence of a drug-resistant virus, thereby allowing the clinician to alter the therapy to one that is more effective. Evidence suggesting that drug resistance testing has clinical utility comes from retrospective and prospective intervention-based studies (Durant et al., 1999, *Lancet* 353:2195-2199; Clevenbergh et al., 1999, *Antiviral Ther.* 4: Abstract 60; Baxter et al., 1999, *Antiviral Ther.* 4: Abstract 61; Cohen et al., 2000, 7$^{th}$ Conference on Retroviruses and Opportunistic Infections (San Francisco, Calif.), Abstract 237). Some mutations known to confer drug resistance affect 20 codons of the protease coding sequence and 27 codons of the reverse transcriptase (RT) coding sequence (Hirsch et al., 2000, *JAMA* 18:2417-2426). A comprehensive list of 190 mutations in pol was reported by Schinazi et al. (*Int'l Antiviral News* 8:65-91 (2000)). Mutations that affect gag cleavage sites have been shown to compensate for loss of enzyme activity due to resistance mutations in protease. Thus, there is a need for genotypic assays that provide sequence information on relevant codons, because such assays may detect a viral mutant which could contribute to drug failure, even if it is a minor component of the patient's viral population.

The HIV-1 genome is highly variable, with three groups (M, O and N) described based on their genetic relatedness. The most prevalent group, M, contains subtypes (A to J), with subtypes A, B and C accounting for about 95% of the viral subtypes found worldwide. Subtype E, which is frequently found in Asia, is a recombinant virus that includes subtype A sequence in the gag and pol genes. Therefore, an effective diagnostic assay must be able to detect at least one of the A, B and C subtypes, and, preferably, all of them.

Detection of HIV-1 by using a variety of assays and reagents has been described previously. For example, U.S. Pat. Nos. 5,594,123, 5,176,995 and 5,008,182 (Sninsky et al.) disclose detection based on the polymerase chain reaction (PCR) to amplify HIV-1 nucleic acid. U.S. Pat. No. 5,688,637 (Moncany et al.) discloses oligonucleotide primer sequences for selected regions of HIV-1 genes, and methods of amplifying viral sequences using the primers and detecting the amplified products. U.S. Pat. No. 5,712,385 (Mc-Donough et al.) and U.S. Pat. No. 5,856,088 (McDonough et al.) disclose amplification oligonucleotides, probes and methods for detecting HIV-1 sequences. U.S. Pat. No. 5,786,177 (Moncany et al.) discloses methods of amplifying HIV-1 nucleotide sequences for gene expression and purification of the polypeptides produced. HIV-1 nucleic acid sequences useful for detecting the presence of HIV-1 have been disclosed in U.S. Pat. No. 5,773,602 and EP 0 178 978 (Alizon et al.), U.S. Pat. No. 5,843,638 (Montagnier et al.), U.S. Pat. No. 6,001,977 (Chang et al.), U.S. Pat. No. 5,420,030 (Reitz et al.) and U.S. Pat. No. 5,869,313 (Reitz et al.), and EP 0 181 150 (Luciw et al.). PCT No. WO 9961666 discloses a method for detecting polymorphic mutations in HIV genetic sequences which provide an indication of an increased risk of an imminent viral drug-resistance mutation.

Methods of amplifying nucleic acids to produce more copies of a target sequence have been described previously. For example, U.S. Pat. Nos. 4,683,195, 4,683,202, and 4,800,159 (Mullis et al.) disclose PCR amplification which uses a thermocycling series of denaturation and polymerization reactions to produce many copies of a target sequence. Amplification methods that rely on transcription using an RNA polymerase have been disclosed in U.S. Pat. Nos. 5,399,491 and 5,554,516 (Kacian et al.), U.S. Pat. No. 5,437,990 (Burg et al.), PCT Nos. WO 8801302 and WO 8810315 (Gingeras et al.), U.S. Pat. No. 5,130,238 (Malek et al.); and U.S. Pat. Nos. 4,868,105 and 5,124,246 (Urdea et al.). The ligase chain reaction (LCR) uses four different oligonucleotides to amplify a target and its complementary strand by using cycles of hybridization, ligation, and denaturation (EP No. 0 320 308). Strand displacement amplification (SDA) uses a primer that contains a recognition site for a restriction endonuclease that nicks one strand of a hemimodified DNA target duplex, followed by primer extension and strand displacement steps (U.S. Pat. No. 5,422,252 (Walker et al.)).

Nucleic acid sequences may be detected by using hybridization with a complementary sequence (e.g., oligonucleotide probes) (see U.S. Pat. No. 5,503,980 (Cantor), U.S. Pat. No. 5,202,231 (Drmanac et al.), U.S. Pat. No. 5,149,625 (Church et al.), U.S. Pat. No. 5,112,736 (Caldwell et al.), U.S. Pat. No. 5,068,176 (Vijg et al.), and 5,202,231 (Macevicz)). Hybridization detection methods may use an array of probes on a DNA chip to provide sequence information about the target nucleic acid which selectively hybridizes to an exactly complementary probe sequence in a set of four related probe sequences that differ one nucleotide (see U.S. Pat. Nos. 5,837,832 and 5,861,242 (Chee et al.)).

SUMMARY OF THE INVENTION

According to one aspect of the invention, there is provided a nucleic acid oligomer for amplifying a nucleotide sequence of HIV-1, comprising a sequence selected from the group consisting of SEQ ID NO:5 to SEQ ID NO:22 and SEQ ID NO:33 to SEQ ID NO:68. In one embodiment, the nucleic acid oligomer has a nucleic acid backbone that includes one or more 2'-O-methoxy linkages, peptide nucleic acid linkages, phosphorothioate linkages, methylphosphonate linkages or any combination of these linkages. In another embodiment, the oligomer is a promoter-primer having a sequence selected from the group consisting of SEQ ID NO:5 to SEQ ID NO:10 and SEQ ID NO:33 to SEQ ID NO:45, wherein a 5' portion of the sequence includes a promoter sequence for T7 RNA polymerase. Another embodiment is a mixture of nucleic acid oligomers that includes oligomers for amplifying a first gag sequence and having a nucleotide sequence selected from the group consisting of SEQ ID NO:5, SEQ ID NO:11, SEQ ID NO:33, SEQ ID NO:35, SEQ ID NO:46, SEQ ID NO:47, SEQ ID NO:17 and SEQ ID NO:59. Another embodiment is a mixture of nucleic acid oligomers includes oligomers for amplifying a second gag sequence and having a nucleotide sequence selected from the group consisting of SEQ ID NO:6, SEQ ID NO:12, SEQ ID NO:34, SEQ ID NO:36, SEQ ID NO:48, SEQ ID NO:49, SEQ ID NO:18, and SEQ ID NO:60. Another mixture embodiment includes oligomers for amplifying a Protease sequence and having a nucleotide sequence selected from the group consisting of SEQ ID NO:7, SEQ ID NO:13, SEQ ID NO:37, SEQ ID NO:38, SEQ ID NO:50, SEQ ID NO:51, SEQ ID NO:19, SEQ ID NO:61, and SEQ ID NO:62. One mixture of oligomers includes oligomers for amplifying a first reverse transcriptase (RT) sequence and having a nucleotide sequence selected from the group consisting of SEQ ID NO:8, SEQ ID NO:14, SEQ ID NO:39, SEQ ID NO:40, SEQ ID NO:41, SEQ ID NO:52, SEQ ID NO:53, SEQ ID NO:54, SEQ ID NO:20, SEQ ID NO:63, SEQ ID NO:64 and SEQ ID NO:65. Another embodiment is a mixture that includes oligomers for amplifying a second RT sequence and having a nucleotide sequence selected from the group consisting of SEQ ID NO:9, SEQ ID NO:15, SEQ ID NO:42, SEQ ID NO:43, SEQ ID NO:55, SEQ ID NO:56, SEQ ID NO:21, and SEQ ID NO:66. Another mixture includes oligomers for amplifying a third RT sequence and having a nucleotide sequence selected from the group consisting of SEQ ID NO:10, SEQ ID NO:16, SEQ ID NO:44, SEQ ID NO:45, SEQ ID NO:57, SEQ ID NO:58, SEQ ID NO:22, SEQ ID NO:67, and SEQ ID NO:68.

Another aspect of the invention is a labeled oligonucleotide that specifically hybridizes to an HIV-1 sequence derived from gag or pol sequences, having a base sequence selected from the group consisting of SEQ ID NO:23 to SEQ ID NO:29, and a label that results in a detectable signal. In one embodiment, the labeled oligonucleotide includes in its nucleic acid backbone one or more 2'-O-methoxy linkages, peptide nucleic acid linkages, phosphorothioate linkages, methylphosphonate linkages or any combination these linkages. In another embodiment, the labeled oligonucleotide includes a label that is a compound that produces a luminescent signal that can be detected in a homogeneous detection system. In one embodiment, the label is an acridinium ester (AE) compound and the oligonucleotide hybridizes to an HIV-1 sequence derived from gag sequences and has a base sequence selected from the group consisting of SEQ ID NO:23, SEQ ID NO:24 and SEQ ID NO:25. In another embodiment, the label is an AE compound and the oligonucleotide hybridizes to an HIV-1 sequence derived from pol sequences and has a base sequence selected from the group consisting of SEQ ID NO:26, SEQ ID NO:27, SEQ ID NO:28, and SEQ ID NO:29.

Another aspect of the invention provides a method of detecting HIV-1 in a biological sample. The method includes the steps of providing a biological sample containing HIV-1 nucleic acid; mixing the sample with two or more amplification oligomers that specifically amplify at least one HIV-1 target sequence contained within gag and pol sequences under conditions that allow amplification of nucleic acid, wherein the amplification oligomers have sequences selected from the group consisting of:

SEQ ID NO:5, SEQ ID NO:11, SEQ ID NO:33, SEQ ID NO:35, SEQ ID NO:46, SEQ ID NO:47, SEQ ID NO:1 7, and SEQ ID NO:59 to amplify a first gag sequence;

SEQ ID NO:6, SEQ ID NO:12, SEQ ID NO:34, SEQ ID NO:36, SEQ ID NO:48, SEQ ID NO:49, SEQ ID NO:18, and SEQ ID NO:60 to amplify a second gag sequence;

SEQ ID NO:7, SEQ ID NO:13, SEQ ID NO:37, SEQ ID NO:38, SEQ ID NO:50, SEQ ID NO:51, SEQ ID NO:19, SEQ ID NO:61 and SEQ ID NO:62 to amplify a first pol sequence, which is a protease sequence;

SEQ ID NO:8, SEQ ID NO:14, SEQ ID NO:39, SEQ ID NO:40, SEQ ID NO:41, SEQ ID NO:52, SEQ ID NO:53, SEQ ID NO:54, SEQ ID NO:20, SEQ ID NO:63, SEQ ID NO:64, and SEQ ID NO:65 to amplify a second pol sequence, which is a first reverse transcriptase (RT) sequence;

SEQ ID NO:9, SEQ ID NO:15, SEQ ID NO:42, SEQ ID NO:43, SEQ ID NO:55, SEQ ID NO:56, SEQ ID NO:21, and SEQ ID NO:66 to amplify a third pol sequence, which is a second RT sequence; and SEQ ID NO:10, SEQ ID NO:16, SEQ ID NO:44, SEQ ID NO:45, SEQ ID NO:57, SEQ ID NO:58, SEQ ID NO:22, SEQ ID NO:67, and SEQ ID NO:68 to amplify a fourth pol sequence, which is a third RT sequence, or a combination of oligomers selected from these groups that allows amplification of at least one gag sequence and at least pol sequence; amplifying the target sequence to produce an amplified nucleic acid product; and detecting the presence of the amplified nucleic acid product. In one embodiment, the amplifying step uses a transcription-mediated amplification method which is conducted in substantially isothermal conditions. In one embodiment, the detecting step uses a labeled oligomer having the sequence of SEQ ID NO:23, SEQ ID NO:24 or SEQ ID NO:25, or a mixture of these oligomers, to hybridize specifically to the amplified nucleic acid produced from a gag sequence; a labeled oligomer having the sequence of SEQ ID NO:26, SEQ ID NO:27, SEQ ID NO:28 or SEQ ID NO:29, or a mixture of these oligomers, to hybridize specifically to the amplified nucleic acid produced from a pol sequence; or a mixture of at least two labeled oligomers, wherein the mixture comprises one or more first labeled oligomers selected from the group consisting of SEQ ID NO:23, SEQ ID NO:24, and SEQ ID NO:25, and one or more second labeled oligomers selected from the group consisting of SEQ ID NO:26, SEQ ID NO:27, SEQ ID NO:28, and SEQ ID NO:29 to hybridize specifically to the amplified nucleic acid produced from at least one gag and at least one pol sequence. Another embodiment of the method has a detecting step that detects hybridization of the amplified nucleic acid to an array of nucleic acid probes. In another embodiment, the method may also include the step of contacting the sample containing HIV-1 nucleic acid with at least one capture oligomer having a sequence that hybridizes specifically to the HIV-1 nucleic acid, thus forming a hybridization complex that includes the HIV-1 nucleic acid, and separating the hybridization complex from other sample components.

The accompanying drawings illustrate some embodiments of the invention. The drawings, together with the description, serve to explain and illustrate the principles of the invention.

DETAILED DESCRIPTION OF THE INVENTION

Figure 1:
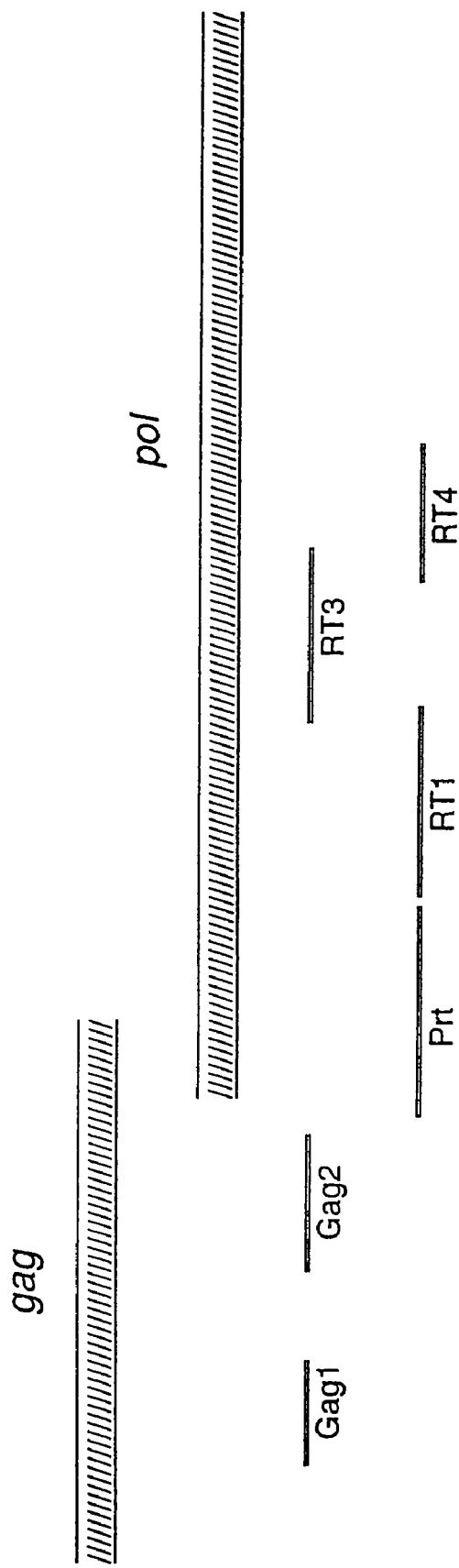
FIG. 1 is a schematic drawing of HIV-1 gag and pol genetic regions (shown left to right in a 5' to 3' orientation at the top) showing the relative positions and sizes of amplified sequences (Gag1, Gag2, Prt, RT1, RT3 and RT4, shown below the gag and pol regions) that are produced using the amplification oligonucleotides and methods of the invention. In one embodiment, the upper group of the Gag1, Gag2 and RT3 regions are amplified in one multiplex reaction, and the lower group of the Prt, RT1 and RT4 regions are amplified in another multiplex reaction.

The present invention includes methods and oligonucleotides to detect HIV-1 nucleic acid in a biological sample, by amplifying one or more HIV-1 target regions and detecting the amplified sequences. The amplified target regions are ones that include many codons that may potentially be mutated when an HIV-1 virus becomes drug resistant. The detection step may be performed using any of a variety of known ways to detect a signal specifically associated with the amplified target sequence, such as by hybridizing the amplification product with a labeled probe and detecting a signal resulting from the labeled probe. The detection step may also may provide additional information on the amplified sequence, such as all or a portion of its nucleic acid base sequence. The compositions and methods of the present invention are useful for detecting the presence of HIV-1 sequences and providing additional information about the infective agent, such as its genetic subgroup or drug-resistance phenotype based on detectable sequence information. Thus, the invention provides useful diagnostic and prognostic information on an HIV-1 infection to a health provider and the patient. In preferred embodiments, multiple different portions of the HIV-1 genome are amplified in a multiplex reaction to produce multiple copies of different HIV-1 sequences in a single reaction vessel. The amplified products from different regions are then detected and/or analyzed further. Multiplex reactions minimize the number of individual reactions that are performed for a sample and, because multiple regions are amplified, multiplex reactions avoid the potential of a false negative result if one region were insufficiently amplified. In one embodiment, the method amplifies multiple different portions of the HIV-1 genome using amplification oligonucleotides in two different multiplex reactions to cumulatively amplify about 2.5 kb of HIV-1 sequence.

The methods of the present invention preferably include amplification using an isothermal transcription-mediated nucleic acid amplification method, as previously disclosed in detail in U.S. Pat. Nos. 5,399,491 and 5,554,516 (Kacian et al.). The methods include a detection step that may use any of a variety of known methods to detect the presence of nucleic acid by hybridization to a probe oligonucleotide. Preferably, the detection step uses a homogeneous detection method such as described in detail previously in Arnold et al. *Clinical Chemistry* 35:1588-1594 (1989), and U.S. Pat. No. 5,658,737 (Nelson et al.), and U.S. Pat. Nos. 5,118,801 and 5,312,728 (Lizardi et al.). The methods of the present invention may also include an optional step of purifying the target HIV-1 from other sample components before amplification, using any of a variety of known purification methods. Methods of purifying nucleic acids are well known in the art (Sambrook et al., *Molecular Cloning, A Laboratory Manual*, $2^{nd}$ ed. (Cold Spring Harbor Laboratory Press, Cold Spring Harbor, N.Y., 1989) at §§ 1.23-1.40, 2.73-2.80, 4.26-4.32 and 7.3-7.35). A preferred embodiment uses a purification step that is relatively fast, involving a minimum of steps, such as a solution phase hybridization disclosed in detail in PCT No. WO 9850583 (Weisburg et al.). Briefly, the purification uses oligonucleotides that hybridize to the target and to immobilized oligonucleotides on a removable solid support, such as magnetic particles (Whitehead et al, U.S. Pat. Nos. 4,554,088 and 4,695,392), to separate the target nucleic acid from other sample components.

The present invention provides methods for detecting HIV-1 nucleic acids present in human biological samples, such as tissue or body fluid samples. A "biological sample" includes any tissue, body fluid or material derived from a living or dead human which may contain HIV-1 nucleic acid, including, for example, peripheral blood, plasma, serum, lymph, bone marrow, cervical swab samples, lymph node tissue, respiratory tissue or exudates, gastrointestinal tissue, urine, feces, semen or other body fluids, tissues or materials.

Using standard methods, the biological sample may be treated to physically or mechanically disrupt tissue or cell structure, to release intracellular components into an aqueous or organic solution to prepare nucleic acids for further analysis.

"Nucleic acid" refers to a multimeric compound comprising nucleosides or nucleoside analogs which have nitrogenous heterocyclic bases, or base analogs, which are linked by phosphodiester bonds to form a polynucleotide. Nucleic acids include conventional RNA and DNA and analogs thereof. The "backbone" of a nucleic acid may be made up of a variety of known linkages, including one or more of sugar-phosphodiester linkages, peptide-nucleic acid bonds (found in "peptide nucleic acids" or "PNA" as described in U.S. Pat. No. 5,539,082 (Nielsen et al.)), phosphorothioate linkages, methylphosphonate linkages or combinations thereof. Sugar moieties may be either ribose or deoxyribose, or known substitutions of such sugars, such as 2' methoxy and 2' halide substitutions (e.g., 2'-F). Nitrogenous bases may be conventional bases (A, G, C, T, U), analogs thereof, e.g., inosine ("I") or nebularine ("N") or synthetic analogs (*The Biochemistry of the Nucleic Acids* 5-36, Adams et al., ed., 11$^{th}$ ed., 1992; Lin & Brown, 1989, *Nucl. Acids Res.* 17:10373-83; Lin & Brown, 1992, *Nucl. Acids Res.* 20:5149-52)), derivatives of purine or pyrimidine bases (e.g., N$^4$-methyl deoxyguanosine, deaza- or aza-purines and deaza- or aza-pyrimidines, pyrimidine bases having substituent groups at the 5 or 6 position, purine bases having a substituent at the 2, 6 or 8 positions, 2-amino-6-methylaminopurine, O$^6$-methylguanine, 4-thio-pyrimidines, 4-aminopyrimidines, 4-dimethylhydrazine-pyrimidines, and O$^4$-alkyl-pyrimidines; see, PCT No. WO 9313121 (Cook)) and "abasic" residues where the polymer backbone includes no nitrogenous base at that position (U.S. Pat. No. 5,585,481 (Arnold et al.)). A nucleic acid may comprise only conventional sugars, bases and linkages, as found in naturally occurring RNA or DNA, or may include a combination of conventional components and substitutions (e.g., conventional bases linked via a 2' methoxy backbone, or a polymer including conventional bases and one or more base analogs).

The backbone composition of an oligomer may affect the stability of a hybridization complex formed between an oligomer and a complementary nucleic acid strand. Embodiments of the oligomers of the present invention may include peptide linkages as in PNA, sugar-phosphodiester linkages, 2' methoxy linkages in part or all of the oligomer, or derivatives thereof. An altered oligomer backbone, relative to standard DNA or RNA, may enhance hybridization complex stability. For example, an oligomer that is a PNA or having 2'-methoxy linkages (containing a 2'-O-methylribofuranosyl moiety; PCT No. WO 98/02582) or 2'-F substituted RNA groups forms a stable hybridization complex with complementary 2' OH RNA. The linkage joining two sugar groups may affect hybridization complex stability by affecting the overall charge or the charge density, or steric interactions. Embodiments of oligomers may include linkages with charged (e.g., phosphorothioates) or neutral (e.g., methylphosphonates) groups to affect complex stability.

The present invention includes amplification oligonucleotides or oligomers to specifically amplify HIV-1 target sequences and probe oligonucleotides or oligomers to detect the HIV-1 target sequences or their amplification products. "Oligonucleotide" and "oligomer" refer to a polymeric nucleic acid having generally less than 1,000 residues, including those in a size range having a lower limit of about 2 to 5 residues and an upper limit of about 500 to 900 residues. In preferred embodiments, oligomers are in a size range having a lower limit of about 5 to about 15 residues and an upper limit of about 100 to 200 residues. More preferably, oligomers of the present invention are in a size range having a lower limit of about 10 to about 15 residues and an upper limit of about 17 to 100 residues. Although oligomers may be purified from naturally occurring nucleic acids, they are generally synthesized using any of a variety of well known enzymatic or chemical methods.

An "amplification oligonucleotide" or "amplification oligomer" is an oligonucleotide that hybridizes to a target nucleic acid, or its complement, and participates in a nucleic acid amplification reaction. Amplification oligomers include primers and promoter-primers in which the oligomer's 3' end is extended enzymatically using another nucleic acid strand as the template. In some embodiments, an amplification oligonucleotide contains at least about 10 contiguous bases, and more preferably about 12 contiguous bases, that are complementary to a region of the target sequence (or its complementary strand), and optionally may contain other bases that do not bind to the target sequence or its complement. For example, a promoter-primer may contain target-binding bases and additional 5' bases that include a promoter sequence that does not hybridize to the target sequence. Contiguous target-binding bases are preferably at least about 80%, and more preferably about 90% to 100% complementary to the sequence to which it binds. An amplification oligomer is preferably about 10 to about 60 bases long and may include modified nucleotides or base analogs.

Embodiments of the present invention use amplification oligomers to specifically amplify regions of the HIV-1 genome, specifically regions the gag and pol genetic sequences. These amplification oligonucleotides include the sequences of SEQ ID NO:5 to SEQ ID NO:22 and SEQ ID NO:33 to SEQ ID NO:68. Some amplification oligomers that are promoter-primers include promoter sequences (SEQ ID NO:5 to SEQ ID NO:10 and SEQ ID NO:33 to SEQ ID NO:45). Preferred T7 promoter sequences included in promoter-primers are shown in SEQ ID NO:1 to SEQ ID NO:4. Those skilled in the art will appreciate that an oligomer that can function as a primer (i.e., one that hybridizes specifically to a target sequence and has a 3' polymerase-extendable end) can be modified to include a 5' promoter sequence, and thus become a promoter-primer. Similarly, any promoter-primer sequence can function as a primer independent of its promoter sequence (such as the sequences shown without promoters in SEQ ID NO:11 to SEQ ID NO:16 and SEQ ID NO:46 to SEQ ID NO:58).

By "amplify" or "amplification" is meant a procedure to produce multiple copies of a target nucleic acid sequence or its complement or fragments thereof (i.e., the amplified product may contain less than the complete target sequence). For example, fragments may be produced by amplifying a portion of the target nucleic acid by using an amplification oligonucleotide which hybridizes to, and initiates polymerization from, an internal position of the target nucleic acid. Known amplification methods include, for example, replicase-mediated amplification, polymerase chain reaction (PCR) amplification, ligase chain reaction (LCR) amplification, strand-displacement amplification (SDA) and transcription-associated or transcription-mediated amplification (TMA). Replicase-mediated amplification uses QB-replicase to amplify RNA sequences (U.S. Pat. No. 4,786,600 (Kramer et al.); PCT No. WO 9014439). PCR amplification uses DNA polymerase, primers for opposite strands and thermal cycling to synthesize multiple copies of DNA or cDNA (U.S. Pat. Nos. 4,683,195, 4,683,202, and 4,800,159 (Mullis et al.); Mullis et al., 1987, *Methods in Enzymology*

155: 335-350). LCR amplification uses at least four different oligonucleotides to amplify complementary strands of a target by using cycles of hybridization, ligation, and denaturation (EP No. 0 320 308). SDA uses a primer that contains a recognition site for a restriction endonuclease and an endonuclease that nicks one strand of a hemimodified DNA duplex that includes the target sequence, followed by a series of primer extension and strand displacement steps (U.S. Pat. Nos. 5,422,252 and 5,470,723 (Walker et al.)). An isothermal strand-displacement amplification method that does not rely on endonuclease nicking is also known (U.S. Pat. No. 6,087,133 (Dattagupta et al.)). Transcription-associated or transcription-mediated amplification uses a primer that includes a promoter sequence and an RNA polymerase specific for the promoter to produce multiple transcripts from a target sequence, thus amplifying the target sequence (U.S. Pat. Nos. 5,399,491, 5,480,784, 5,824,518 and 5,888,779 (Kacian et al.), U.S. Pat. No. 5,437,990 (Burg et al.), U.S. Pat. No. 5,409,818 (Davey et al.), U.S. Pat. Nos. 5,554,516 and 5,766,849 (McDonough et al.), U.S. Pat. No. 5,130,238 (Malek et al.), U.S. Pat. Nos. 4,868,105 and 5,124,246 (Urdea et al.), and U.S. Pat. No. 5,786,183 (Ryder et al.)), PCT Nos. WO 8801302 and WO 8810315 (Gingeras et al.)).

Preferred embodiments of the present invention amplify the HIV-1 target sequences using the present amplification oligomers in a transcription-mediated amplification (TMA) reaction. One skilled in the art will appreciate that these amplification oligonucleotides can readily be used in other methods of nucleic acid amplification that uses polymerase-mediated primer extension.

"Transcription-mediated amplification" refers to nucleic acid amplification that uses an RNA polymerase to produce multiple RNA transcripts from a nucleic acid template. The amplification reaction employs an RNA polymerase, a DNA polymerase, an RNase H activity, ribonucleoside triphosphates, deoxyribonucleoside triphosphates, and a promoter-primer, and may include one or more additional amplification oligonucleotides. Preferred embodiments use the methods disclosed in detail in U.S. Pat. Nos. 5,399,491, 5,480,784, 5,824,518 and 5,888,779 (Kacian et al.), U.S. Pat. Nos. 5,554,516 and 5,766,849 (McDonough et al.), and U.S. Pat. No. 5,786,183 (Ryder et al.)).

Following amplification of the HIV-1 target sequences, the amplified products are detected using hybridization to probes that allow detection of a hybridization complex formed between the amplified sequence and the probe oligonucleotide sequence. In some embodiments, the probe is labeled and the signal detected from the hybridization complex is produced from the labeled probe. In other embodiments, amplified products are labeled and hybridized to a probe and the detected signal is produced from the labeled product in the hybridization complex. In embodiments which provide sequence information in the detection step, the amplified nucleic acid is hybridized to an array of oligonucleotide probes (U.S. Pat. Nos. 5,837,832 and 5,861,242 (Chee et al.)) and the detected signals are analyzed using a computerized system (U.S. Pat. Nos. 5,733,729 and 6,066,454 (Lipshutz et al.)), to produce a nucleic acid sequence from "base calls" by the system.

A "probe" refers to a nucleic acid oligomer that hybridizes specifically to a nucleic acid target sequence, under conditions that promote hybridization, thereby allowing detection of the target sequence. Detection may either be direct (i.e., resulting from a probe hybridizing directly to the target sequence) or indirect (i.e., resulting from a probe hybridizing to an intermediate molecular structure that links the probe and target sequences). The "target sequence" of a probe refers to a sequence within a nucleic acid, preferably in an amplified nucleic acid, which hybridizes specifically to at least a portion of a probe oligomer. A probe may comprise target-specific sequences and other sequences that contribute to a probe's three-dimensional conformation (see U.S. Pat. Nos. 5,118,801 and 5,312,728 (Lizardi et al.)). Sequences that are "sufficiently complementary" allow stable hybridization of a probe oligomer to its target sequence under hybridization conditions, even if the probe and target sequences are not completely complementary by standard base pairing (G:C, A:T or A:U pairing). "Sufficiently complementary" probe sequences may contain one or more residues (including abasic residues) that are not 100% complementary, but which, due to the probe's entire base sequence are capable of specifically hybridizing with another sequence in the hybridization conditions. Appropriate hybridization conditions are well known in the art, can be predicted readily based on base sequence composition, or can be determined empirically by using routine testing (e.g., see Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57). In preferred embodiments, probes include contiguous bases that are at least about 80%, more preferably at least about 90%, and most preferably about 100% complementary to the target sequence.

For detection, the probe may be labeled, i.e., joined directly or indirectly to a detectable molecular moiety or a compound that leads to a detectable signal. Direct labeling can occur through bonds or interactions that link the label to the probe, including covalent bonds and non-covalent interactions (e.g. hydrogen bonding, hydrophobic and ionic interactions), or formation of chelates or coordination complexes. Indirect labeling occurs through use of a bridging moiety (a "linker"), that joins a label to the probe, and which can amplify a detectable signal (e.g., see PCT No. WO 95/16055 (Urdea et al.)). Labels are well known and include, for example, radionuclides, ligands (e.g., biotin, avidin), enzymes and/or enzyme substrates, reactive groups, redox active moieties such as transition metals (e.g., Ru), chromophores (e.g., a moiety that imparts a detectable color), luminescent compounds (e.g., bioluminescent, phosphorescent or chemiluminescent labels) and fluorescent compounds. Those skilled in the art will appreciate that a labeled probe may be a mixture of labeled and unlabeled oligonucleotides that hybridize specifically to the target sequence, to optimize the specific activity of the probe reagent for detection. In some embodiments, the label on a probe is detectable in a homogeneous assay system, i.e., in a mixture, bound labeled probe exhibits a detectable change, such as stability or differential degradation, compared to unbound labeled probe. A preferred label for use in a homogenous assay is a chemiluminescent compound (U.S. Pat. No. 5,656,207 (Woodhead et al.), U.S. Pat. No. 5,658,737 (Nelson et al.), and U.S. Pat. No. 5,639,604 (Arnold, Jr., et al.)). Preferred chemiluminescent labels include acridinium ester ("AE") compounds, which may be standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE). Methods of attaching labels to nucleic acids and detecting labels are well known in the art (e.g., see Sambrook et al., *Molecular Cloning, A Laboratory Manual,* 2nd ed. (Cold Spring Harbor Laboratory Press, Cold Spring Harbor, N.Y., 1989), Chapter 10, U.S. Pat. No. 5,658,737 (Nelson et al.), U.S. Pat. No. 5,656,207 (Woodhead et al.), U.S. Pat. No. 5,547,842 (Hogan et al.), and U.S. Pat. No. 5,283,174 (Arnold, Jr. et al.), and PCT No. WO 9802582 (Becker)).

Methods of the present invention may optionally include a step of purifying the HIV-1 target nucleic acid from other sample components before amplification. By "purifying" is meant that the target is separated from one or more components of the biological sample (e.g., other nucleic acids, proteins, carbohydrates or lipids). Preferably, a purifying step removes at least about 70%, and more preferably about 90% or more of the other sample components. In embodiments that include such a purification step, the HIV-1 target nucleic acid is hybridized to a "capture oligomer" that specifically joins the HIV-1 target sequence to an immobilized oligomer (i.e., attached to a solid support) based on nucleic acid hybridization, as previously described in detail (PCT No. WO 98/50583). This step is advantageous because it involves two solution-phase hybridizations (hybridization of the capture oligomer and the target, followed by hybridization of the target:capture oligomer complex to the immobilized oligomer to produce a target:capture oligomer:immobilized oligomer complex) that permit rapid separation of the target from the other sample components.

By "consisting essentially of" is meant that additional component(s), composition(s) or method step(s) that do not materially change the basic and novel characteristics of the present invention may be included in the compositions or methods of the present invention. Such characteristics include the ability to amplify and detect HIV-1 sequences present in a sample.

Unless defined otherwise, all scientific and technical terms used herein have the same meaning as commonly understood by those skilled in the relevant art. General definitions of many of the terms used herein are provided, for example, in *Dictionary of Microbiology and Molecular Biology,* 2nd ed. (Singleton et al., 1994, John Wiley & Sons, New York, N.Y.). Unless otherwise described, the techniques employed or contemplated herein are standard methods well known to one of ordinary skill in the art. The examples illustrate some of the preferred embodiments.

The present invention includes nucleic acid oligomers and methods for detecting HIV-1 nucleic acid present in a human biological sample. To determine appropriate DNA sequences for use as amplification oligomers, known HIV-1 sequences, generally of known subtypes and including partial or complementary sequences available from publicly accessible databases (e.g., GenBank), were aligned by matching regions of the same or similar sequences and compared using well known molecular biology techniques. Although use of algorithms may facilitate sequence comparisons, those skilled in the art can readily perform such comparisons without the aid of an algorithm. Amplification oligomers were designed that would amplify portions of the HIV-1 gag and pol genes (based on the sequence of HIV-1 HXB2, GenBank Acc. No. KO 3455) provided that: the oligomer sequences do not contain known drug-resistance mutations, the oligomer combinations each amplify about 300 to 600 nt, the oligomers contain a minimum of predicted secondary structure based on well-known methods for predicting nucleic acid structure, the sequences contain few known polymorphic bases (intra- or inter-subtype polymorphisms) and, for residues in which polymorphisms occur, that the base found in the majority of compared sequences for that position or a base analog (e.g., nebularine) is used at that position. Sequence comparisons used in designing amplification oligomers, generally were: for gag region, 22 subtype A, 41 subtype B 12 subtype C, 11 subtype D, 6 subtype F, 4 subtype G, 3 subtype H, and 2 subtype J sequences; for the Protease region, 22-34 subtype A, 36-41 subtype B, 15 subtype D, 26 subtype F, and 8 subtype G sequences; and for the RT region, 32-44 subtype A, 38-46 subtype B, 24 subtype C, 9-15 subtype D, 5-26 subtype F, and 8 subtype G sequences.

Probe oligomers were similarly designed, selecting for sequences complementary to those that occur within the amplified sequences. DNA oligomers were synthesized using well known synthetic methods and tested for their efficiency as amplification or probe oligomers. Labeled probes were labeled with an AE compound attached via a linker, substantially as described in detail in U.S. Pat. No. 5,639,604 (see column 10, line 6 to column 11, line 3, and Example 8). The efficiency of oligomers was tested in the amplification and detection systems described herein, and in some cases, oligomer sequences were modified to optimize amplification or detection, e.g., by changing one or more residues, substituting a base analog, or by modifying part or all of the oligomer backbone (e.g., substituting 2'-O-methyl RNA for DNA).

Based on these analyses, the amplification oligonucleotides described herein were identified. Amplification oligonucleotides may optionally include a promoter sequence for producing transcripts from amplified target sequences, and preferred T7 promoter sequences are shown in SEQ ID NO:1 to SEQ ID NO:4. For amplification oligomers that include a T7 promoter sequence, the primer sequences have been shown with the T7 promoter sequence (SEQ ID NO:5 to SEQ ID NO:10 and SEQ ID NO:33 to SEQ ID NO:45) and without a T7 promoter sequence (SEQ ID NO:11 to SEQ ID NO:16 and SEQ ID NO:46 to SEQ ID NO:58). Those skilled in the art will appreciate that a amplification oligomer specific for HIV-1, with or without a promoter sequence, may be useful as a primer under appropriate amplification conditions.

Figure 2:
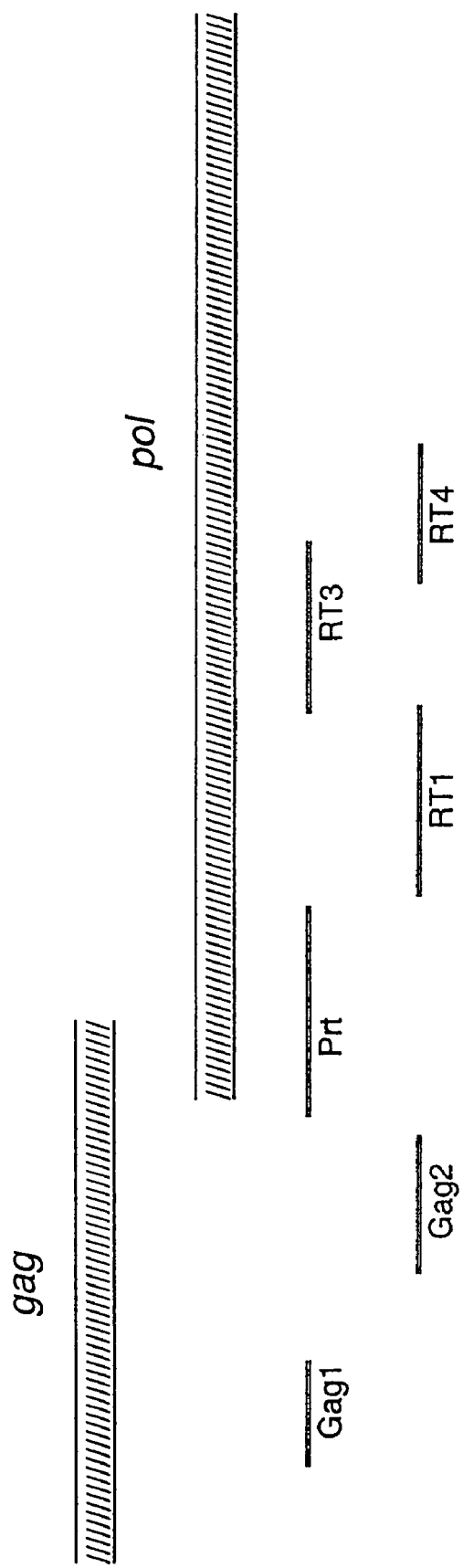
FIG. 2 is a schematic drawing of HIV-1 gag and pol regions and amplified sequences as described in FIG. 1, but in this embodiment, the upper group of the Gag1, Prt and RT3 regions are amplified together in one multiplex reaction, and the lower group of the Gag2, RT1 and RT4 regions are amplified in another multiplex reaction.

Referring to FIGS. 1 and 2, the upper portion illustrates the gag and pol regions of the HIV-1 genome (shaded overlapping regions labeled gag and pol) and the lower portion shows the approximate sizes and locations of the regions (double lines labeled underneath as Gag1, Gag2, Prt, RT1, RT3 and RT4) amplified using the amplification primers. These amplified regions include the characteristics: Gag1 contains the cleavage site between Gag P24 and Gag P17; Gag2 contains other Gag cleavage sites; Prt contains two cleavage sites at the 3' end of Gag, the protease region and the cleavage site between protease and reverse transcriptase (RT); RT1 contains codons between 41 and 190 of RT; RT3 contains codons between 200 and 350 of RT; and RT4 contains codons at the 3' end of RT and the cleavage site between RT and RNase H. FIGS. 1 and 2 illustrate the relative sizes and locations of the amplified regions, although the absolute sizes of amplified regions may vary slightly depending on the particular combination of amplification oligomers used. For example, Gag sequences amplified using primers having the sequences of SEQ ID NO:5 and SEQ ID NO:17 produce a 260 nt amplification product (Gag1), and SEQ ID NO:6 and SEQ ID NO:18 produce a 415 nt amplification product (Gag2). The protease (Prt) region amplified using the primers having the sequences of SEQ ID NO:7 and SEQ ID NO:19 produce a 574 nt amplification product. Three reverse transcriptase (RT) sequences of the pol gene result from amplification using primers having the sequences of: SEQ ID NO:8 and SEQ ID NO:20 to produce a 532 nt product (RT1), SEQ ID NO:9 and SEQ ID NO:21 to produce a 464 nt product (RT3), and SEQ ID NO:10 and SEQ ID NO:22 to produce a 384 nt product (RT4). Other combinations of related amplification oligomer sequences can similarly be used to amplify these regions, for example: for Gag1 (SEQ ID NO:33 and SEQ ID NO:17 or SEQ ID NO:59), for Gag2 (SEQ ID NO:34 or SEQ ID NO:36 and SEQ ID NO:60), for Prt (SEQ ID NO:37 or SEQ ID NO:38 and SEQ ID NO:19, SEQ ID NO:61 or SEQ ID NO:62), for RT1 (SEQ ID NO:39, SEQ ID NO:40 or SEQ ID NO:41 and SEQ ID NO:20, SEQ ID NO:63, SEQ ID NO:64 or SEQ ID NO:65), for RT3 (SEQ ID NO:42 or SEQ ID NO:43 and SEQ ID NO:66), and for RT4 (SEQ ID NO:44 or SEQ ID NO:45 and SEQ ID NO:67 or SEQ ID NO:68). In preferred embodiments, the amplification oligomers of SEQ ID NO:18 to SEQ ID NO:22, and SEQ ID NO:35 include 2'-O-methoxy linkages for the backbone of one or more 5' residues, preferably for residues 1 to 4.

For detection of the amplified target sequences, probe sequences complementary to the amplified sequences were designed, and preferred embodiments of such probes have the sequences of SEQ ID NO:23 to SEQ ID NO:29, SEQ ID NO:69 and SEQ ID NO:70. More specifically, a probe of SEQ ID NO: 23 hybridizes to Gag1 amplification products or amplicons, a probe of SEQ ID NO: 24 hybridizes to Gag1 amplicons produced from an HIV-1 subtype A template, probes of SEQ ID NO:25 and SEQ ID NO:69 hybridize to Gag2 amplicons, a probe of SEQ ID NO: 26 hybridizes to Prt amplicons, probes of SEQ ID NO: 27 and SEQ ID NO:70 hybridize to RT1 amplicons, a probe of SEQ ID NO: 28 hybridizes to RT3 amplicons, and a probe of SEQ ID NO: 29 hybridizes to RT4 amplicons. Any backbone may be used to link the base sequence of a probe oligomer, and some embodiments include one or more 2'-O-methoxy linkages, e.g., for SEQ ID NO:24 to SEQ ID NO:29, SEQ ID NO:69 and SEQ ID NO:70. When used as labeled probes, the probe oligomers may include any known detectable label or label that leads to production of a detectable signal. In some embodiments, the probe oligomers are labeled with an acridinium ester (AE) compound via a linker as described previously (U.S. Pat. No. 5,639,604 (Arnold, Jr. et al.)). For example, some embodiments of the probes were labeled as follows: SEQ ID NO:23 between residues 9 and 10, SEQ ID NO:24 between residues 10 and 11, SEQ ID NO:25 between residues 17 and 18, SEQ ID NO:26 between residues 9 and 10, SEQ ID NO:27 between residues 16 and 17, SEQ ID NO:28 between residues 9 and 10, SEQ ID NO:29 between residues 10 and 11, SEQ ID NO:69 between residues 11 and 12, and SEQ ID NO:70 between residues 11 and 12.

For those embodiments that use a capture oligomer to purify the HIV-1 target from other sample components, the capture oligomer sequences were a combination of SEQ ID NO:30, SEQ ID NO:31 and SEQ ID NO:32. These capture probes include a 5' portion of the sequence that specifically hybridizes with an HIV-1 sequence (pol or LTR sequences) and a 3' poly-A "tail" portion that hybridizes with a complementary immobilized oligomer ($dT_{14}$) on a solid support (e.g., paramagnetic particles). Those skilled in the art will appreciate that any 3' portion that binds to a complementary immobilized sequence may be used in place of the poly-dA tail and any backbone that permits hybridization may be used to link the base sequence of a capture oligomer.

Using these components, an assay to detect HIV-1 sequences in a biological sample includes the steps of optionally purifying the target HIV-1 nucleic acid from a sample using one or more capture oligomers, amplifying the target HIV-1 region using at least two primers, preferably by using a transcription-mediated amplification reaction, and detecting the amplified nucleic acid by hybridizing the amplified nucleic acid with one or more probes that hybridize specifically to the amplified nucleic acid. If the detection step uses a labeled probe, then the a signal resulting from the bound labeled probe is detected. If the detection step uses hybridization to an array of probes attached to a solid support (a "DNA chip"), then the amplification product may be labeled before it is hybridized to the DNA chip for detection of probe loci that specifically bind to the amplified product. Amplicons may be labeled as part of the amplification step or after amplification. A preferred method for labeling the amplicons after amplification also fragments the product into smaller portions for detection on a DNA chip (see PCT No. WO 00/65926 and PCT No. PCT/IB99/02073 for details).

If an optional purification step before amplification is used, it is preferably performed in a single reaction vessel using a minimum of handling steps, such as by using the two-step hybridization procedure described in PCT No. WO 98/50583. Briefly, a capture oligomer is added to a sample containing HIV-1 target nucleic acid under a first hybridizing condition in which one portion of the capture oligomer specifically hybridizes to the HIV-1 target sequence, producing a capture oligomer:HIV-1 RNA complex. Then, under a second hybridizing condition, a second portion of the capture probe hybridizes to a complementary oligomer sequence immobilized on a solid support such as a magnetic bead, producing an immobilized oligomer:capture oligomer:HIV-1 RNA complex. For both hybridization conditions, the sample is in a mixture of salts, detergent and buffer (e.g., 400 mM HEPES, 1-10% lithium lauryl sulfate (LLS), 240-832 mM LiOH, 0-783 mM LiCl, pH 7.6-8.0), the capture oligomer(s), and immobilized oligomers on solid particles, and the two different hybridization conditions are obtained by incubating at a first and a second temperature. Then the solid support with the attached immobilized oligomer:capture oligomer:HIV-1 RNA complex is physically separated from other sample components to purify the target HIV-1 RNA. The solid support with the attached nucleic acid complex can be washed using standard methods (e.g., rinsing with a buffered aqueous solution under conditions that allow the nucleic acid complex to remain hybridized), to further purify the HIV-1 RNA. If magnetic particles are the solid support, physical separation can readily be accomplished by application of a magnetic field to the vessel. Following purification, the HIV-1 RNA-containing complex attached to the support may be used directly in amplification.

Amplifying the HIV-1 target using two or more amplification oligomers can be accomplished using a variety of known nucleic acid amplification reactions that rely on primer extension to produce multiple copies of the target sequence or its complement. One embodiment uses transcription-mediated amplification substantially as described in detail previously (U.S. Pat. Nos. 5,399,491, 5,480,784, 5,554,516, 5,766,849, 5,786,183, 5,824,518, and 5,888,779). Briefly, transcription-mediated amplification uses two primers (one being a promoter-primer that contains a promoter sequence for an RNA polymerase), a DNA polymerase (a reverse transcriptase), an RNA polymerase, and nucleosides (deoxyribonucleoside triphosphates, ribonucleoside triphosphates) with appropriate salts and buffers in solution to produce multiple RNA transcripts from a nucleic acid template. Initially, a promoter-primer (also referred to as a P1 primer) hybridizes specifically to the target sequence and the reverse transcriptase creates a first strand cDNA by extension of the 3' end of the promoter-primer, and its RNase H activity digests the RNA target strand in the RNA:cDNA complex. The first strand cDNA hybridizes with the second primer (also referred to as a P2 primer) at a location 3' of the promoter-primer sequence and the reverse transcriptase creates a new DNA copy by extension of the 3' end of the P2 primer, thereby creating a double-stranded DNA having a functional promoter sequence at one end. RNA polymerase binds to the functional promoter sequence and transcribes it to produce multiple transcripts (which are amplification products or amplicons). Each transcript can serve as a template for another cycle of replication, i.e., the P2 primer binds to the amplicon, and reverse transcriptase creates a cDNA to which the P1 promoter binds and reverse transcriptase make a double-stranded DNA with a functional promoter at one end which binds the RNA polymerase to produce more transcripts. Thus, under substantially isothermal conditions, transcription-mediated amplification produces many amplicons, i.e., about 100 to about 3,000 RNA transcripts from a single template. Although embodiments described in the examples use P1 promoter-primers that include a promoter sequence recognized by T7 RNA polymerase, those skilled in the art will appreciate that any combination of a promoter sequence and its corresponding RNA polymerase may be used (e.g., T3 polymerase).

Amplification reaction mixtures for transcription-mediated amplification generally contain 1-2.5 mM $Mg^{+2}$, 18-40 mM Tris (pH 8), 0.5-3.5 mM ATP, 1.75-7.0 mM UTP, 5-16 mM GTP, 1.75-5.6 mM CTP, 0.75 mM dNTP, 25-37.5 mM KCl, optimized amounts of each primer, 2600-3000 U reverse transcriptase and 2600-3600 U T7 RNA polymerase. A typical reaction mixture includes 1 mM $Mg^{+2}$, 32.5 mM Tris (pH 8), 0.5-1.0 mM ATP, 5.0 mM UTP, 5-9 mM GTP, 5 mM CTP, 0.75 mM dNTP, 37.5 mM KCl, primers, and 3000 U each of reverse transcriptase and T7 RNA polymerase.

Detecting the amplification products may use any step that detects specific hybridization of amplicon to one or more probe sequences. If a labeled probe hybridizes to the amplicons, the label is preferably one that can be detected in a homogeneous system (i.e., one that does not require unbound probe to be separated from the amplicon:probe complexes for detection of bound probes). In some embodiments, the label is an AE compound from which produces a chemiluminescent signal that is detected, as described in detail previously (U.S. Pat. Nos. 5,283,174, 5,656,744 and 5,658,737). Alternatively, amplicons or fragments thereof may be hybridized to an array of probes as on a DNA chip and those probes that specifically hybridize to the amplicons are detected to provide sequence information about the HIV-1 target from which the amplicons were produced. Those skilled in the art will appreciate that more than one procedure may be used to detect the amplification products produced from a single amplification reaction. For example, a portion of the amplification reaction may be subjected to a labeled probe hybridization procedure to provide a positive or negative response, indicating the presence or absence of HIV-1 specific amplification products in the reaction, thereby indicating that the sample was positive or negative for HIV-1. For reactions that test positive, another, portion of the amplification reaction may be further assayed using hybridization to a DNA probe array to provide sequence information on the HIV-1 present in the sample, thereby providing further more detailed diagnostic information.

Although any one of the gag and pol regions amplified by using the disclosed amplification oligomers may be detected to supply diagnostic information about the sample, amplification and detection of more than one region potentially provides more diagnostic information, for example, by detecting multiple genetic markers associated with drug-resistance. Individual gag and pol regions may be amplified separately and the amplicons then pooled for detection, but to simplify the assay multiple regions were amplified in multiplex reactions. That is, each multiplex reaction includes multiple amplification oligomers to amplify multiple HIV-1 target regions in a single reaction vessel.

Multiplex reactions were designed to amplify multiple target sequences while avoiding potential interference between amplification oligomers for hybridization to their respective target sequences or production of relatively small amplicons. For example, referring to FIG. 1, the target regions labeled RT1 and RT3 overlap, as do the RT3 and RT4 target regions. Thus, a relatively small target region could be amplified if a multiplex reaction included amplification oligomers for the overlapping targets, e.g., from use of the combination of SEQ ID NO:9 or SEQ ID NO:15 (P1 primers for RT3) and SEQ ID NO:22 (P2 primer for RT4). Therefore, multiplex reactions were designed to include primer combinations that will not produce small amplicons which would not provide much diagnostic information but would consume substrates during amplification. Different combinations of amplification oligomers were tested in multiplex reactions, including (1) amplification oligomers to amplify the Gag1, RT1 and RT4 target regions in one vessel and amplification oligomers to amplify the Gag2, Prt and RT3 target regions in another vessel, (2) amplification oligomers to amplify the Gag1, Gag2 and RT3 target regions in one vessel and amplification oligomers to amplify the Prt, RT1 and RT4 target regions in another vessel (illustrated in FIG. 1), and (3) amplification oligomers to amplify the Gag2, RT1 and RT4 target regions in one vessel and amplification oligomers to amplify the Gag1, Prt and RT3 target regions in another vessel (illustrated in FIG. 2). Each of the reactions of these multiplex combinations amplifies over 1 kb of HIV-1 target nucleic acid and the combined two multiplex reactions for each combination cumulatively amplify over 2.5 kb of HIV-1 sequence.

Some embodiments of the present invention are illustrated by the examples that follow. In these examples, the HIV-1 RNA used in nucleic acid amplification was from virus present in supernatants of lymphocyte cultures infected with virus subtypes A, B or C, purified HIV-1 RNA isolated from culture supernatants, transcripts produced from cloned HIV-1 sequences, or plasmas obtained from patients infected with HIV-1, where the viral subtype was determined by sequencing or by antigens present in the viral envelop of viruses in the plasma.

EXAMPLE 1

Amplification and Detection of a Gag Target Sequence from Different Subtypes of HIV-1

Samples were prepared containing known amounts of HIV-1 RNA from three different subtypes (A, B and C), which were then amplified using primers specific for the Gag1 target region in a transcription-mediated amplification reaction. Following amplification, the amplification products were detected by using two different labeled probes for the Gag 1 amplicons and a mixture of the two different labeled probes.

In the first test HIV-1 subtype B RNA was mixed with water to achieve 500 copies per reaction tube, and HIV-1 subtype A viral supernatant was mixed with a buffer (400 mM HEPES, pH 7.6, 10% (w/v) lithium lauryl sulfate (LLS), 350 mM LiOH, 783 mM LiCl) to achieve 500 copies per reaction tube. For amplification, each reaction contained the sample and 7.5 pmol each of the amplification oligomers having SEQ ID NO:5 (a T7 primer-promoter or P1 primer) and SEQ ID NO:17 (a P2 primer) in a reaction mixture (40 mM Tris, pH 7.5, 17.5 mM KCl, 20 mM $MgCl_2$, 5% polyvinylpyrrolidone, 1 mM each dNTP, 4 mM each rNTP). The reaction mixtures were covered with a layer (200 µl) of inert oil to prevent evaporation, and incubated at 60° C. for 10-15 min, and then at 41.5-42° C. for 5 min. For each reaction mixture, about 3000 U each of reverse transcriptase and T7 RNA polymerase were added, mixed, and the target HIV-1 nucleic acid was amplified at 41.5-42° C. for 2 hr.

Following amplification, detection of the amplified Gag target region was detected by using AE-labeled probes having SEQ ID NO:23, SEQ ID NO:24 or a mixture of these probes (0.05-0.1 pmol each), and chemiluminescence was detected from bound probes using previously described methods (U.S. Pat. No. 5,658,737 at column 25, lines 27-46; Nelson et al., 1996, *Biochem.* 35:8429-8438 at 8432). The detected chemiluminescence was expressed in relative light units (RLU). Negative controls were similarly treated but contained no HIV-1 target nucleic acid.

Table 1 presents the detected RLU results for each probe (mean of triplicate assays, except one negative control assay for the "Probe Mixture"). These results show that both subtypes of HIV-1 were amplified using the amplification oligomers for the Gag1 target region but the probe of SEQ ID NO:23 only detected amplified Gag1 products from subtype B, whereas the probe of SEQ ID NO:24 detected amplified products from both subtypes A and B. The results obtained using the probe mixture appear to be additive of the results obtained with the individual probes for the two subtypes.

TABLE 1

Amplification and Detection (RLU) of HIV-1 Subtype A and Subtype B Gag1 Target Region

| HIV-1 Subtype | SEQ ID NO: 23 Probe | SEQ ID NO: 24 Probe | Probe Mixture |
|---|---|---|---|
| A | $1.12 \times 10^4$ | $5.55 \times 10^6$ | $5.67 \times 10^6$ |
| B | $5.13 \times 10^6$ | $4.55 \times 10^6$ | $9.04 \times 10^6$ |
| Negative Control | $1.31 \times 10^4$ | Not determined | $2.25 \times 10^4$ |

In another test, similar assays were performed using HIV-1 subtypes A, B and C at 250, 50 or 25 copies of virus RNA per reaction, and using the probe mixture (SEQ ID NO:23 and SEQ ID NO:24). For subtypes B and C, HIV-1 RNA was the target, and, for subtype A, viral supernatant contained the target nucleic acid. Table 2 presents the results of this test (mean RLU for 6 samples for each condition). The negative controls, i.e., no HIV-1 target present, produced $1.37 \times 10^4$ RLU (mean of duplicate assays).

TABLE 2

Detection of Amplified Gag1 Target Region By Using a Labeled Probe Mixture

| HIV-1 Subtype | 250 Copies of Target | 50 Copies of Target | 25 Copies of Target |
|---|---|---|---|
| A | $4.73 \times 10^6$ | $2.80 \times 10^6$ | $8.76 \times 10^5$ |
| B | $2.79 \times 10^6$ | $1.77 \times 10^6$ | $1.52 \times 10^6$ |
| C | $4.51 \times 10^6$ | $4.46 \times 10^6$ | $1.78 \times 10^6$ |

These results show that the amplification oligonucleotides amplified the Gag1 target region for HIV-1 subtypes A, B and C and the probes detected the amplified sequences. The assay system had a sensitivity of at least 50 copies of target for all of the subtypes. At 25 copies of target per reaction, all of the subtypes were amplified and detected (producing at least 10-fold more RLU than the negative controls) in at least half of the reactions (data not shown). These results show that HIV-1 can be readily detected in a biological sample using the methods of the present invention.

Similar experiments were performed using the combinations of amplification oligomers for each of the other individual target sequences amplified (Gag2, Prt, RT1, RT3 and RT4). Probe oligomers were also hybridized specifically to each of their respective targets in similar homogeneous detection assays to produce detectable luminescent signals proportional to the amount of amplified product produced in the amplification reaction.

EXAMPLE 2

Sensitivity of Detection of HIV-1 Target Sequences of Subtypes A, B and C

This example shows that the amplification oligomers can effectively amplify target sequences from the three subtypes of HIV-1 that are most prevalent throughout the world, subtypes A, B, and C. In these experiments, HIV-1 target RNA was used in transcription-mediated amplification reactions at 25, 50, 100, 250, 500 or 1000 copies per reaction, obtained from viral RNA, RNA transcripts from cloned HIV-1 sequences or virus present in plasma. The individual target regions (Gag1, Gag2, Prt, RT1, RT3 and RT4) were amplified in separate reactions and detected by hybridization with AE-labeled probes using substantially the conditions described in Example 1. The results (RLU for each subtype) of some of these experiments are shown in Table 3 (reporting average RLU obtained from at least triplicate reactions, except for the Prt results reported for plasma virus detection which were results from one test). The sensitivity is shown by the number of copies of the target (for the different sources of virus ("V"), transcript ("T") or infected plasma ("P")) present in the sample which were amplified.

TABLE 3

Sensitivity of Detection of Amplified HIV-1 Target Regions Using AE-labeled Probes

| Target | Primers | Subtype A (copies & source) | Subtype B (copies & source) | Subtype C (copies & source) |
|---|---|---|---|---|
| Gag1 | SEQ ID NO: 5 | $7.1 \times 10^6$ (100 T) | $4.3 \times 10^6$ (50 T) | $1.8 \times 10^6$ (25 V) |
| | SEQ ID NO: 17 | $2.8 \times 10^6$ (50 V) | $1.5 \times 10^6$ (25 V) | |

TABLE 3-continued

Sensitivity of Detection of Amplified HIV-1 Target Regions Using AE-labeled Probes

| Target | Primers | Subtype A (copies & source) | Subtype B (copies & source) | Subtype C (copies & source) |
|---|---|---|---|---|
| Prt | SEQ ID NO: 7 | $2.2 \times 10^6$ (500 T) | $3 \times 10^6$ (250 T) | $1.7 \times 10^6$ (250 T) |
|  | SEQ ID NO: 19 | $3 \times 10^6$ (100 P) | $5.9 \times 10^6$ (100 V) | $>3.5 \times 10^6$ (100 P) |
|  |  |  | $>3 \times 10^6$ (500 P) |  |
| RT4 | SEQ ID NO: 10 | $2.1 \times 10^6$ (50 T) | $3.8 \times 10^6$ (50 T) | $5.7 \times 10^6$ (50 T) |
|  | SEQ ID NO: 22 | $>2.5 \times 10^6$ (25 V) | $>2.2 \times 10^6$ (25 V) | $>3.6 \times 10^6$ (25 V) |

These results show that for all three subtypes, the sensitivity of detection was at least 100 copies of target, and often was less than 100 copies (e.g., 25-50 copies of virus for Gag1 for all three subtypes). Similar results were obtained for the other HIV-1 target regions (data not shown), all having a sensitivity of detection of at least 200 copies of target for the three subtypes in most of the assays performed using the amplification oligomers and detection probes of this invention.

EXAMPLE 3

Detection of HIV-1 Target Sequences in Multiplex Reactions

In this experiment, two separate multiplex reactions, each amplifying three HIV-1 target regions were used to show that the individual target regions can be amplified to produce detectable amplicons. Each amplification tube contained 200 copies of HIV-1 subtype B RNA and amplification reagents substantially as described in Example 1. Amplification tube 1 contained primers to amplify the Gag2, RT1 and RT4 regions (SEQ ID NO:6 and SEQ ID NO:18, SEQ ID NO:8 and SEQ ID NO:20, including a 3' blocked oligomer of SEQ ID NO:8, and SEQ ID NO:10 and SEQ ID NO:22). Amplification tube 2 contained primers to amplify the Gag1, Prt and RT3 regions (SEQ ID NO:5 and SEQ ID NO:17, SEQ ID NO:7 and SEQ ID NO:19, and SEQ ID NO:9 and SEQ ID NO:21). The amounts per reaction of each of these primers were as follows: in tube 1, 4 pmol each of SEQ ID NO:6, SEQ ID NO:10, SEQ ID NO:18 and SEQ ID NO:22, 2.4 pmol of SEQ ID NO:8, 12 pmol of SEQ ID NO:20 and 9.6 pmol of 3' blocked SEQ ID NO:8; and in tube 2, 1 pmol of SEQ ID NO:5, 4 pmol of SEQ ID NO:17, 4.5 pmol of SEQ ID NO:7, 5 pmol each of SEQ ID NO:9 and SEQ ID NO:19, and 9.85 pmol of SEQ ID NO:21. For each set of reactions, five individual tubes were prepared and amplified. Amplification reactions were performed substantially as described in Example 1, and then half of the reaction (i.e., the equivalent of amplicons produced from 100 copies of target HIV-1 RNA) was used in the detection step.

Detection was performed using AE labeled probes using the homogeneous detection assay substantially as described previously (U.S. Pat. No. 5,658,737 at column 25, lines 27-46; Nelson et al., 1996, Biochem. 35:8429-8438 at 8432) and chemiluminescence was detected as RLU for each amplification reaction and for each probe using a calibrated luminometer (LEADER® HC450, Gen-Probe Incorporated, San Diego, Calif.). The labeled probes used (0.1 pmol/reaction) were: SEQ ID NO:24 to detect Gag1, SEQ ID NO:69 to detect Gag2, SEQ ID NO:26 to detect Prt, SEQ ID NO:70 to detect RT1, SEQ ID NO:28 to detect RT3 and SEQ ID NO:29 to detect RT4. To optimize the specific activities of the probes for detection, the probe reagents generally were a mixture of labeled and unlabeled probes for each of the probe oligomers.

The results of these tests, reported as the mean of the five reactions for each condition, are shown in Table 4 (negative controls are not shown). These results show that all three of the target sequences were amplified in each of the multiplex reactions to produce amplicons that were specifically detected by their corresponding probes specific for the amplified sequences.

TABLE 4

Multiplex Amplification Reaction Products Detected by Labeled Probe Hybridization (RLU)

| Tube 1 | | |
|---|---|---|
| Gag2 | RT1 | RT4 |
| $2.5 \times 10^6$ | $1.4 \times 10^6$ | $6.3 \times 10^5$ |
| Tube 2 | | |
| Gag1 | Prot | RT3 |
| $1.5 \times 10^5$ | $8.5 \times 10^5$ | $1.6 \times 10^6$ |

In other experiments, different ratios of amplification oligomers were used in the same multiplex combinations as tested above to provide similar amplification results. For example, another multiplex combination used the following amounts of primers per reaction tube 1: 4 pmol each of SEQ ID NO:6, SEQ ID NO:10, and SEQ ID NO:22, 3 pmol of SEQ ID NO:18, 2.4 pmol of SEQ ID NO:8, 9.6 pmol each of SEQ ID NO:20 and 3' blocked SEQ ID NO:8.

EXAMPLE 4

Detection of HIV-1 Target Sequences from Clinical Samples

This example describes detection of HIV-1 target sequences present in biological samples taken from HIV-1 patients whose symptoms indicate that the infection has become drug resistant (viral rebound during drug treatment). Multiplex amplification reactions were used to produce amplified nucleic acid from multiple targets in a single reaction tube for detection. The method detected amplified products hybridized to an array of DNA probes to provide amino acid information at residues commonly associated with HIV-1 drug resistance in the Gag, Protease and RT regions.

Plasma was collected from three HIV-positive patients being treated with combinations of drugs who were experiencing increased viral load. Patients 1 and 2 were both being treated with one drug combination (d4T, 3TC and NELFINAVIR™) and had viral loads of 6,130 and 10,000 copies/ml, respectively; Patent 3 was treated with another drug combination (ABACAVIR™, EFAVIRENZ™ and NELFINAVIR™) and had a viral load of 10,000 copies/ml. From each patient, 0.5 ml of plasma was dispensed into two separate tubes and mixed with 0.5 ml of lysis buffer (0.4 M HEPES, pH 7.6, 0.35 M LiOH, 0.22 M LLS) and incubated at 60° C. for 20 min. Released viral RNA was purified from other sample components by hybridization to three capture oligonucleotides added to the mixture (3.5 pmol/test of each of SEQ ID NO:30 and SEQ ID NO:32, and 10 pmol/test of SEQ ID NO:31) and dT$_{14}$ oligonucleotides immobilized on magnetic particles; the mixture was incubated at 55-60° C. for 15-20 min and then at 18-25° C. for 10-15 min. The magnetic particles were pelleted using a magnetic field and unbound sample components were aspirated away; the magnetic particles with bound HIV-1 RNA were washed twice (1.5 ml of washing buffer). The washed particles were suspended in 75 µl of amplification buffer (50 mM HEPES, pH 7.5, MgCl$_2$, KCl, glycerol, dATP, dCTP, dGTP, dTTP, ATP, CTP, GTP, UTP and amplification oligonucleotides). The amplification oligonucleotides for each target region were: SEQ ID NO:33 and SEQ ID NO:17 for Gag1; SEQ ID NO:34 and SEQ ID NO:60 for Gag2; SEQ ID NO:41 and SEQ ID NO:19 for Protease; SEQ ID NO:41 and SEQ ID NO:20 for RT1; SEQ ID NO:9 and SEQ ID NO:21 for RT3; and SEQ ID NO:10 and SEQ ID NO:22 for RT4. Amplification reaction tube 1 contained primers for amplifying the Gag1, Protease and RT3 targets; and amplification reaction tube 2 contained primers for amplifying the Gag2, RT1 and RT4 targets. Amplification reaction mixtures were incubated at 60° C. for 10 min and then about 3000 U each of reverse transcriptase and T7 RNA polymerase were added (in 25 µl of 8 mM HEPES, pH 7.5, 170 mM Tris, 70 mM KCl, 0.01% Phenol Red, 10% TRITON® X-100, 0.08% TRITON® X-102, 20% glycerol, 0.04 mM EDTA, 50 mM N-acetyl L-cysteine, 0.04 mM Zn-acetate, 0.08% trehalose) and the mixture was incubated for 1 hr at 42° C.

The amplification reactions were pooled for each patient (50 µl from each of tubes 1 and 2) and the amplified products were labeled using previously described methods (PCT No. WO 99/65926 and PCT/IB99/02073). Briefly, the amplification products were mixed with labeling reagent (final concentration of 60 mM MnCl$_2$, 6 mM imidazole, 2 mM bromofluorescein in 150 µl total volume) and incubated at 60° C. for 30 min, and then 15 µl of 0.5 M EDTA was added. Labeled nucleic acids were purified using standard column chromatography (QIAVAC™, Qiagen, SA, Courtaboeuf, France) and eluted in a 100 µl volume which was mixed with 400 µl of hybridization buffer (0.06 M HEPES, pH 7.5, 0.9 M NaCl, 3 M betaine, 5 mM DTAB, 500 ug/ml salmon sperm DNA, 0.06% antifoam, $5 \times 10^{-4}$ nmol/test of control oligonucleotide). The mixture was incubated with an array of immobilized DNA probes for 30 min at 35° C. (DNA-CHIP™ in a Fluidic Station, Affymetrix, Inc., Santa Clara, Calif.; Lipshutz et al., *BioFeature* 3:442-447(1995); U.S. Pat. No. 5,744,305). Unbound material was washed from the array twice (using a HEPES, NaCl, TRITON® X-102 solution) and the hybridization results on the array were detected to determine the relevant HIV-1 sequences present in the patient samples (Lipshutz et al., *BioFeature* 3:442-447 (1995); PCT No. WO 95/11995). This system can detect 1005 polymorphic HIV-1 gag and pol sequences covering 180 mutations associated with drug-resistance (drug resistance codons determined by French Agence Nationale de la Recherche sur le SIDA). For the detection step, the fluorescence intensity was measured for each probe site on the array (using an Affymetrix confocal laser reader), and an algorithm (Affymetrix GENECHIP™ software) was used to determine the base corresponding to the most intense signal which was used to determine the amino acid(s) likely to be present for a the codon. The predicted amino acids at selected positions obtained using this method for each of the three patient samples is shown, using the single letter amino acid code, in Table 5 for the RT codons and in Table 6 for Protease codons ("Chip" columns). For comparison, the HIV-1 sequence for each patient sample was determined independently (using standard sequencing methods following RT-PCR as described in U.S. Pat. No. 5,795,722), and the predicted amino acids for each of the codons corresponding to those determined by hybridization analysis are shown in the tables ("Seq" columns). For each reported position, the wild-type (non-drug-resistance) amino acid is shown in the first column ("WT & position"); "nd" means not determined.

These results show that the amplified HIV-1 sequences hybridized to the DNA probes provided information on mutations affecting amino acids associated with drug resistance (mutations shown in bold), and that the hybridization results generally agreed with the predicted amino acids determined by sequencing for 135 analyzed codons (98.5%). In two cases, probe hybridization detected a mutant sequence whereas DNA sequencing detected a mixture of wild-type and mutant sequences. Detection of the mutant, however, is clinically important for diagnosis.

TABLE 5

RT Codons Predicted from Amplified HIV-1 RNA from Three Patients

| WT & Position | Patient 1 | | Patient 2 | | Patient 3 | |
|---|---|---|---|---|---|---|
| | Chip | Seq | Chip | Seq | Chip | Seq |
| M41 | M | M | L | L | L | L |
| A62 | A | A | A | A | A | A |
| K65 | K | K | K | K | nd | K |
| D67 | D | D | N | N | N | N |
| S68 | S | S | S | S | S | S |
| T69 | T | T | T | T | T | T |
| K70 | K | K | K | K | R | R |
| L74 | L | L | L | L | V | V |
| V75 | V | V | V | V | V | V |
| F77 | F | F | F | F | F | F |
| A98 | A | A | A | A | A | A |
| L100 | L | L | L | L | L | L |
| K101 | K | K | E | E | K | K |
| K103 | K | K | K | K | R | R |
| V106 | V | V | V | V | V | V |
| V108 | V | V | V | V | V | V |
| Y115 | Y | Y | Y | Y | Y | Y |
| F116 | F | F | F | F | F | F |
| Q151 | Q | Q | Q | Q | Q | Q |
| Y181 | Y | Y | Y | Y | Y | Y |
| M184 | V | V | V | V | M | M |
| Y188 | Y | Y | Y | Y | Y | Y |
| G190 | G | G | G | G | A | A |
| L210 | L | L | L | L | W | W |
| T215 | T | T | Y | Y | Y | Y |
| K219 | K | K | Q | Q | E | E |
| P225 | P | P | P | P | P | P |
| P236 | P | P | P | P | P | P |

TABLE 6

Protease Codons Predicted from Amplified HIV-1 RNA from Three Patients

|  | Patient 1 | | Patient 2 | | Patient 3 | |
|---|---|---|---|---|---|---|
| WT & Position | Chip | Seq | Chip | Seq | Chip | Seq |
| L10 | L | L | I | L/I | L | L |
| K20 | K/I/M | K/I/M | K | K | R | R |
| D30 | D | D | nd | D | D | D |
| M36 | M | M | M | M | I | I |
| M46 | M | M | nd | M | M | M |
| I47 | I | I | I | I | I | I |
| G49 | G | G | G | G | G | G |
| I50 | I | I | I | I | I | I |
| I54 | I | I | I | I | I | I |
| L63 | P | P | P | P | P | P |
| A71 | A | A | A | A | A | I |
| G73 | S | G/S | S | S | G | G |
| V77 | I | I | I | I | V | V |
| V82 | V | V | V | V | V | V |
| I84 | I | I | I | I | V | V |
| N88 | N | N | N | N | N | N |
| L90 | M | M | M | M | M | M |

In other experiments, amplification of HIV-1 target sequences was similarly performed to produce detectable products using the following combinations of amplification oligomers: for Gag1 (SEQ ID NO:33 and SEQ ID NO:59), for Gag2 (SEQ ID NO:36 and SEQ ID NO:60), for Prt (SEQ ID NO:37 or SEQ ID NO:38 and SEQ ID NO:19, SEQ ID NO:61 or SEQ ID NO:62), for RT1 (SEQ ID NO:39 or SEQ ID NO:40 and SEQ ID NO:20, SEQ ID NO:63, SEQ ID NO:64 or SEQ ID NO:65), for RT3 (SEQ ID NO:42 or SEQ ID NO:43 and SEQ ID NO:66), and for RT4 (SEQ ID NO:44 or SEQ ID NO:45 and SEQ ID NO:67 or SEQ ID NO:68).

EXAMPLE 5

PCR Amplification and Detection of Amplified HIV-1 Protease and RT1 Target Sequences In this example, HIV-1 target sequences (Prt and RT1) were amplified using the reverse transcriptase-polymerase chain reaction (RT-PCR) and the amplified sequences were then detected by using the DNA chip analysis as described in the previous example, compared to standard DNA sequencing. Viral RNA was purified from tissue culture supernatant of 92BR020 isolate (from The National Institutes of Health, Bethesda, Md.) using standard RNA purification methods (QIAMP™ Viral RNA Mini Kit, Qiagen, SA, Courtaboeuf, France) to produce an eluate containing 5×10$^5$ copies/ml. RT-PCR was performed using standard methods (ACCESS™ RT-PCR Kit, Promega, Madison, Wis.) using the primers described in the previous example for amplification of the Prt and RT1 target sequences (for Prt, SEQ ID NO:37 and SEQ ID NO:19; for RT1, SEQ ID NO:41 and SEQ ID NO:20), performed in separate tubes. After amplification, the results were checked using electrophoresis through a 1.5% agarose gel stained with ethidium bromide, relative to standard molecular size markers. A band of amplified nucleic acid of the expected size was seen for RT1 for tubes containing 5 copies/ml of target and for Protease for tubes containing 500 copies/ml of target.

Following amplification, an aliquot from each tube was sequenced using standard DNA sequencing methods. For hybridization to a DNA probe array on a chip, 10 µl of the amplified material was used as a template for transcription using T7 RNA polymerase in standard procedures (AMBION MEGASCRIPT™ T7 kit, Cliniscences, Montrouge, France). Following transcription, 8 µl of RNA products were labeled with bromofluorescein substantially as described in the previous example. The predicted amino acid results for various positions of the Prt and RT1 amplified sequences are shown in Table 7, presented as described in the previous example.

These results show that the amplification oligomers can produce amplicons by using another amplification method (RT-PCR) and that the products, or transcripts produced from the amplification products, provide sequence information relevant to mutations by hybridization to a probe array and by sequencing. The results were in generally in agreement (91.1%) for the 45 codons analyzed.

TABLE 7

Predicted Amino Acids from Protease and RT1 Amplified Sequences

| Protease WT & Position | 92BR020 Chip | 92BR020 Seq | RT1 WT & Position | 92BR020 Chip | 92BR020 Seq |
|---|---|---|---|---|---|
| L10 | L | L | M41 | M | M |
| K20 | nd | K | A62 | A | A |
| D30 | D | D | K66 | K | K |
| M36 | I | I | D67 | D | D |
| M46 | M | M | S68 | S | S |
| I47 | I | I | T69 | T | T |
| G48 | G | G | K70 | K | K |
| I50 | I | I | L74 | nd | L |
| I54 | I | I | V75 | V | V |
| L63 | L | L | F77 | F | F |
| A71 | A | A | A98 | A | A |
| G73 | G | G | L100 | L | L |
| V77 | V | V | K101 | K | K |
| V82 | V | V | K103 | K | K |
| I84 | I | I | V106 | nd | V |
| N88 | nd | N | V108 | V | V |
| L90 | L | L | Y115 | Y | Y |
| | | | F116 | F | F |
| | | | Q151 | Q | Q |
| | | | Y181 | Y | Y |
| | | | M184 | M | M |
| | | | Y188 | Y | Y |
| | | | G190 | G | G |

The invention is defined by the claims that follow and includes all legally equivalent embodiments of the claimed invention.

We claim:

1. A mixture of nucleic acid oligomers for amplifying a nucleotide sequence of HIV-1 in a gag region referred to as a first gag sequence, comprising a sequence selected from the group consisting of SEQ ID NO:5, SEQ ID NO:17, SEQ ID NO:33, SEQ ID NO:35, SEQ ID NO:46, SEQ ID NO:47, and SEQ ID NO:59.

2. A nucleic acid oligomer according to claim 1, wherein the oligomer nucleic acid backbone comprises one or more 2'-methoxy linkages, peptide nucleic acid linkages, phosphorothioate linkages, methylphosphonate linkages or any combination of these linkages.

3. A nucleic acid oligomer according to claim 1, wherein the oligomer is a promoter-primer comprising a sequence selected from the group consisting of SEQ ID NO:5, SEQ ID NO:33, and SEQ ID NO:35, wherein a 5' portion of the sequence includes a promoter sequence for T7 RNA polymerase.

4. A mixture of nucleic acid oligomers according to claim 1, wherein the mixture further comprises oligomers for amplifying a second gag sequence and having a nucleotide sequence selected from the group consisting of SEQ ID NO:18, and SEQ ID NO:60.

5. A mixture of nucleic acid oligomers according to claim 1, wherein the mixture further comprises oligomers for amplifying a Protease sequence and having a nucleotide sequence selected from the group consisting of SEQ ID NO:7, SEQ ID NO:13, SEQ ID NO:37, SEQ ID NO:38, SEQ ID NO:50, SEQ ID NO:51, SEQ ID NO:19, SEQ ID NO:61, and SEQ ID NO:62.

6. A mixture of nucleic acid oligomers according to claim 1, wherein the mixture further comprises oligomers for amplifying a first reverse transcriptase (RI) sequence and having a nucleotide sequence selected from the group consisting of SEQ ID NO:8, SEQ ID NO:14, SEQ ID NO:39, SEQ ID NO:40, SEQ ID NO:41, SEQ ID NO:52, SEQ ID NO:53, SEQ ID NO:54, SEQ ID NO:20, SEQ ID NO:63, SEQ ID NO:64 and SEQ ID NO:65.

7. A mixture of nucleic acid oligomers according to claim 1, wherein the mixture further comprises oligomers for amplifying a second RT sequence and having a nucleotide sequence selected from the group consisting of SEQ ID NO:9, SEQ ID NO:15, SEQ ID NO:42, SEQ ID NO:43, SEQ ID NO:55, SEQ ID NO:56, SEQ ID NO:21, and SEQ ID NO:66.

8. A mixture of nucleic acid oligomers according to claim 1, wherein the mixture further comprises oligomers for amplifying a third RI sequence and having a nucleotide sequence selected from the group consisting of SEQ ID NO:10, SEQ ID NO:16, SEQ ID NO:44, SEQ ID NO:45, SEQ ID NO:57, SEQ ID NO:58, SEQ ID NO:22, SEQ ID NO:67, and SEQ ID NO:68.

9. A mixture of nucleic acid oligomers according to claim 1, wherein the mixture further comprises a labeled oligonucleotide that specifically hybridizes to an HIV-1 sequence derived from the first gag sequence, having a base sequence selected from the group consisting of SEQ ID NO:23 and SEQ ID NO:24, and a label that results in a detectable signal.

10. A labeled oligonucleotide according to claim 9, wherein the oligonucleotide includes in its nucleic acid backbone one or more 2'-methoxy linkages, peptide nucleic acid linkages, phosphorothioate linkages, methylphosphonate linkages or any combination of these linkages.

11. A labeled oligonucleotide according to claim 9, wherein the label is a compound that produces a luminescent signal that can be detected in a homogeneous detection system.

12. A labeled oligonucleotide according to claim 9, wherein the label is an acridinium ester (AE) compound.

13. A mixture of nucleic acid oliogmers according to claim 1, further comprising a labeled oligonucleotide that hybridizes to an HIV-1 sequence derived from pc/sequences and has a base sequence selected from the group consisting of: SEQ ID NO:26, SEQ ID NO:27, SEQ ID NO:28, and SEQ ID NO:29, and a labeled oligonucleotide that hybridizes to an HIV-1 sequence derived from a second gag sequence and has the base sequence of SEQ ID NO:25.

14. A method of detecting HIV-1 in a biological sample, comprising the steps of:
providing a biological sample containing HIV-1 nucleic acid;
mixing the sample with two or more amplification oligomers that specifically amplify at least one HIV-1 target sequence contained within a first gag sequence under conditions that allow amplification of nucleic acid, wherein the amplification oligomers have sequences selected from the group consisting of:
SEQ ID NO:5, SEQ ID NO:33, SEQ ID NO:35, SEQ ID NO:46, SEQ ID NO:47, SEQ ID NO:17, and SEQ ID NO:59 to amplify a first gag sequence;
amplifying the target sequence in the first gag sequence to produce an amplified nucleic acid product; and
detecting the presence of the amplified nucleic acid product.

15. The method of claim 14, wherein the amplifying step uses a transcription-mediated amplification method which is conducted in substantially isothermal conditions.

16. The method of claim 14, wherein the detecting step uses:
a labeled oligomer having the sequence of SEQ ID NO:23, SEQ ID NO:24, or a mixture of these oligomers, to hybridize specifically to the amplified nucleic acid product of the first gag sequence.

17. The method of claim 14, wherein the detecting step detects hybridization of the amplified nucleic acid to an array of nucleic acid probes.

18. The method of claim 14, further comprising the step of contacting the sample containing HIV-1 nucleic acid with at least one capture oligomer having a sequence that hybridizes specifically to the HIV-1 nucleic acid, thus forming a hybridization complex that includes the HIV-1 nucleic acid and separating the hybridization complex from other sample components.

19. The method of claim 14, wherein the detecting step detects hybridization of the amplified nucleic acid product to a labeled oligonucleotide that is labeled with a compound that produces a luminescent signal that can be detected in a homogeneous detection system.

20. The method of claim 14, wherein at least one amplification oligomer includes a nucleic acid backbone that comprises one or more 2'-methoxy linkages.

21. The method of claim 14, wherein the mixing step further includes mixing two or more amplification oligomers that specifically amplify at least one HIV-1 target sequence contained within a HIV-1 pol sequence, wherein the amplifying step further amplifies a pol target sequence to produce an amplified nucleic acid product of the pol sequence, and wherein the detecting step detects the amplified nucleic acid product of the pol sequence.

22. The method of claim 21, wherein the detecting step detects hybridization of the amplified nucleic acid product of the pol sequence to at least one nucleic acid probe specific for the pol sequence.

23. The method of claim 14, wherein the mixing step further includes mixing two or more amplification oligomers that specifically amplify at least one HIV-1 target sequence contained within a HIV-1 second gag sequence, wherein the amplifying step further amplifies a second gag target sequence to produce an amplified nucleic acid product of the second gag sequence, and wherein the detecting step detects the amplified nucleic acid product of the second gag sequence.

24. The method of claim 23, wherein the detecting step detects hybridization of the amplified nucleic acid product of the second gag sequence to at least one nucleic acid probe specific for the second gag sequence.

* * * * *